(12) United States Patent
Yamada et al.

(10) Patent No.: US 8,310,678 B2
(45) Date of Patent: Nov. 13, 2012

(54) ANALYZING DEVICE AND ANALYZING METHOD

(75) Inventors: Ryosuke Yamada, Ehime (JP); Masahiro Aga, Ehime (JP); Koji Miyoshi, Ehime (JP); Kenji Murakami, Ehime (JP); Hideyuki Kurokawa, Ehime (JP); Takahiko Tanida, Ehime (JP)

(73) Assignee: Panasonic Corporation, Osaka (JP)

( * ) Notice: Subject to any disclaimer, the term of this patent is extended or adjusted under 35 U.S.C. 154(b) by 251 days.

(21) Appl. No.: 12/864,439

(22) PCT Filed: Jan. 22, 2009

(86) PCT No.: PCT/JP2009/000219
§ 371 (c)(1),
(2), (4) Date: Jul. 23, 2010

(87) PCT Pub. No.: WO2009/093453
PCT Pub. Date: Jul. 30, 2009

(65) Prior Publication Data
US 2010/0290051 A1  Nov. 18, 2010

(30) Foreign Application Priority Data

Jan. 25, 2008 (JP) ................. 2008-014328
Feb. 14, 2008 (JP) ................. 2008-032500
Nov. 28, 2008 (JP) ................. 2008-304128

(51) Int. Cl.
*G01N 21/55* (2006.01)
*G01N 21/47* (2006.01)

(52) U.S. Cl. ...................... 356/445; 356/446
(58) Field of Classification Search ............... None
See application file for complete search history.

(56) References Cited

U.S. PATENT DOCUMENTS 4,729,657 A   3/1988  Cooper et al.
2007/0046713 A1  3/2007  Miyahara et al.

FOREIGN PATENT DOCUMENTS

| JP | 63-5240 | 1/1988 |
| JP | 7-5110 | 1/1995 |
| JP | 09-133628 | 5/1997 |
| JP | 10-142053 | 5/1998 |
| JP | 2002-335538 | 11/2002 |
| JP | 2005-227107 | 8/2005 |
| JP | 2006-292582 | 10/2006 |
| JP | 2007-93586 | 4/2007 |

OTHER PUBLICATIONS

International Search Report of PCT/JP2009/000219, dated Apr. 21, 2009.

*Primary Examiner* — Gregory J Toatley
*Assistant Examiner* — Amanda Merlino
(74) *Attorney, Agent, or Firm* — Hamre, Schumann, Mueller & Larson, P.C.

(57) ABSTRACT

Provided is a device in which light from a sample 7 fixed in a test piece 1 is captured by an image sensor 5 through an optical system made up of a lens 3, a diaphragm 4, and so on and concentration information is obtained, wherein a wideband light source 12 for illuminating the test piece 1 is combined with an optical filter 13 for optionally selecting a wavelength of the light captured by the image sensor. Thus it is possible to reduce a measurement error caused by a change of the light quantity distribution of the light source 12.

2 Claims, 29 Drawing Sheets

ANALYZING DEVICE AND ANALYZING METHOD

TECHNICAL FIELD

The present invention relates to an analyzing device and an analyzing method in which a photo detector element and an image sensor are used, and specifically relates to a technique of reducing a measurement error in the analyzing device and the analyzing method.

BACKGROUND ART

FIG. 21 shows the configuration of an analyzing device of the prior art in which light from a sample set on a test piece is captured by a photo detector element through an optical system and concentration information is obtained. In the analyzing device of the prior art, light from a light source 2 such as an LED is emitted to a test piece 1 on which the sample is set. Further, scattered light, transmitted light, or reflected light from the test piece 1 is captured by the photo detector element such as an image sensor 5 through the optical system that is made up of a lens 3, a diaphragm 4, and so on. The concentration of a sample 7 set on the test piece 1 is quantified by a received light quantity 6 of the photo detector element (e.g., see Japanese Patent Laid-Open No. 7-5110).

As shown in FIGS. 22A to 22C, in this analyzing device, a received light quantity distribution 10 (see FIG. 22C) of the photo detector element is determined by the product of a light quantity distribution 8 (see FIG. 22A) of the light source 2 relative to a detected wavelength and a scattered light (transmitted light or reflected light) characteristic 9 (see FIG. 22B) of the sample 7. In this case, when the light quantity distribution 8 of the light source 2 does not fluctuate, the concentration of the sample 7 may be calculated by the received light quantity of the photo detector element and the calculated concentration may be used as a measured value. Generally, the light source 2 is a narrow-range light source such as a monochromatic LED.

DISCLOSURE OF THE INVENTION

Problems to be Solved by the Invention

In the analyzing device of FIG. 21, however, the light quantity distribution 8 of the light source 2 is changed by factors such as a temperature change and a current change of the light source 2 as shown in FIGS. 23A to 23C (for example, when the light source 2 is an LED, the light quantity distribution 8 shifts in a short wavelength direction as the temperature or current amount of the light source 2 increases). Thus when the temperature or current of the light source 2 fluctuates, the received light quantity of the photo detector element also changes, causing an error of a measured value (for example, when the light of the light source 2 shifts in the short wavelength direction as previously mentioned, the received light quantity of the photo detector element and the measured value are reduced). As the band of the light quantity distribution 8 of the light source 2 decreases and a change of the light quantity distribution 8 of the light source 2 increases, a change of the received light quantity of the photo detector element increases, resulting in a large measurement error.

The present invention has been devised to solve the problem of the analyzing device of the prior art. An object of the present invention is to provide an analyzing device that can reduce a measurement error even when the light quantity distribution of a light source is changed relative to a wavelength by factors such as a temperature change and a current change.

Another object of the present invention is to provide an analyzing method and an analyzing device that can reduce a measurement error caused by the dependence of an optical filter on an incident angle, and an analyzing method and an analyzing device that can reduce a measurement error by making a correction according to the concentration of a sample.

Means for Solving the Problems

In order to solve the problem of the prior art, an analyzing device of the present invention in which light from a sample set on a test piece is captured by a photo detector element through an optical system including a lens and a diaphragm and the concentration information of the sample is obtained, the analyzing device including: a wide-band light source for illuminating the test piece; and an optical filter for optionally selecting a wavelength of the light captured by the photo detector element.

In this configuration, the wide-band light source with a wide-band wavelength is used as a light source for illuminating the test piece. Thus as compared with a narrow-range light source such as a monochromatic light source, the wide-band light source generally has a small change in the light quantity distribution relative to a wavelength of the light source. By using the wide-band light source and selecting, through the optical filter, a wavelength of the light captured by the photo detector element, it is possible to suppress a change in the received light quantity of the photo detector element and reduce an error of a measured value even when the light quantity distribution of the light source is changed relative to a wavelength by factors such as a temperature change and a current change.

Further, according to the present invention, the light from the sample has a wavelength characteristic changing relative to a wavelength, and a quantity of light from the wide-band light source relative to a wavelength has a wavelength characteristic opposite or substantially opposite from the light from the sample.

With this configuration, by combining the light quantity distribution of the light source relative to a detected wavelength and the wavelength characteristics of the sample, it is possible to generate a wavelength band with no change or a small change in the wavelength characteristic. Therefore, even when the light quantity distribution of the light source is changed by factors such as a temperature change and a current change, it is possible to minimize a change in the received light quantity of the photo detector element and reduce an error of a measured value.

According to the present invention, the wide-band light source has a wavelength characteristic with a small change in light quantity relative to a wavelength.

According to the present invention, the optical filter can select only a wavelength band having a constant change or a small change relative to a wavelength.

An analyzing method of the present invention in which light from a sample set on a test piece is received by an image sensor having multiple pixels through an optical system having an optical filter and the concentration information of the sample is obtained, the analyzing method including: a filter incident angle detecting step of detecting the filter incident angle of light incident on the optical filter, the light forming an image on the pixel; a shift amount obtaining step of obtaining the shift amount of the filter band of the optical filter according to the filter incident angle; a correction coefficient setting step of setting a correction coefficient according to the shift amount; a correcting step of correcting one of a luminance value and a value equivalent to the luminance value by using the correction coefficient; and a concentration obtaining step of obtaining the concentration information of the sample based on the value corrected in the correcting step.

An analyzing device of the present invention in which light from a sample set on a test piece is received by an image sensor having multiple pixels through an optical system having an optical filter and the concentration information of the sample is obtained, the analyzing device including: a filter incident angle detector for detecting the filter incident angle of light incident on the optical filter, the light forming an image on the pixel; a shift amount obtaining unit for obtaining the shift amount of the filter band of the optical filter according to the filter incident angle; a correction coefficient setting unit for setting a correction coefficient according to the shift amount; a correcting unit for correcting one of a luminance value and a value equivalent to the luminance value by using the correction coefficient; and a concentration obtaining unit for obtaining the concentration information of the sample based on the value corrected by the correcting unit.

According to the analyzing method and the analyzing device, the sample set on the test piece is imaged by the image sensor. Even when light transmitted to the pixel of the image sensor forms an incident angle (inclined) relative to the optical filter, the shift amount of the filter band of the optical filter is obtained according to the incident angle of the light transmitted to the pixel, the shift amount corresponding to the filter incident angle, the correction coefficient is obtained, and the concentration information of the sample is satisfactorily corrected, thereby reducing a measurement error caused by the dependence of the optical filter on an incident angle.

An analyzing method of the present invention in which light from a sample set on a test piece is received by an image sensor having multiple pixels through an optical system having an optical filter and the concentration information of the sample is obtained, the analyzing method including: a first step of calculating beforehand a luminance value obtained at any position in the image sensor based on the dependence on a filter incident angle and the wavelength characteristics of the light from the sample set with various known concentrations on the test piece; a second step of calculating correction coefficients for matching luminance distributions obtained at the respective concentrations in the first step with the luminance distribution of any reference concentration selected from the concentrations; a third step of making a rectilinear approximation by plotting the correction coefficients obtained at the respective concentrations in the second step, relative to the concentration information; a fourth step of calculating the correction function of the dependence on a filter incident angle according to the reference concentration, based on the luminance distribution of the reference concentration; a fifth step of correcting luminance obtained on the samples separately set to be measured with unknown concentrations on the test piece, by using the correction function obtained in the fourth step according to the reference concentration, and calculating the concentration information by using the corrected luminance; a sixth step of obtaining the concentration correction coefficients of the samples to be measured, by correlating the concentration information obtained in the fifth step with a straight line determined in the third step; and a seventh step of integrating the concentration correction coefficients obtained in the sixth step to the correction function obtained in the fourth step according to the reference concentration, correcting the luminance of the samples to be measured, by using the correction functions after the integration, and obtaining again the concentration information of the samples to be measured, by using the corrected luminance.

An analyzing device of the present invention in which light from a sample set on a test piece is received by an image sensor having multiple pixels through an optical system having an optical filter and the concentration information of the sample is obtained, the analyzing device including: a luminance calculator for calculating a luminance value beforehand at any position in the image sensor based on the dependence on a filter incident angle and the wavelength characteristics of the light from the sample set with different known concentrations on the test piece; a first correction coefficient calculator for calculating correction coefficients for matching luminance distributions obtained at the respective concentrations by the luminance calculator with the luminance distribution of any reference concentration selected from the concentrations; a rectilinear approximation unit for making a rectilinear approximation by plotting the correction coefficients obtained at the respective concentrations by the first correction coefficient calculator, relative to the concentration information; a correction function calculator for calculating the correction function of the dependence on a filter incident angle according to the reference concentration, based on the luminance distribution of the reference concentration; a concentration calculator for correcting luminance obtained on the samples separately set to be measured with unknown concentrations on the test piece, by using the correction function obtained by the correction function calculator according to the reference concentration, and calculating the concentration information by using the corrected luminance; a second correction coefficient obtaining unit for obtaining the concentration correction coefficients of the samples to be measured, by correlating the concentration information obtained by the concentration calculator with a straight line determined by the rectilinear approximation unit; and a concentration obtaining unit for integrating the concentration correction coefficients obtained by the second correction coefficient obtaining unit to the correction function obtained by the correction function calculator according to the reference concentration, correcting the luminance of the samples to be measured, by using the correction functions after the integration, and obtaining again the concentration information of the samples to be measured, by using the corrected luminance.

Advantages of the Invention

According to the analyzing device of the present invention, a wide-band light source with a wide-band wavelength is used as a light source for illuminating a test piece and the wavelength of light captured by a photo detector element is selected by an optical filter.

Thus even the light quantity distribution of the light source changes relative to a wavelength by factors such as a temperature change and a current change, it is possible to suppress a change in the received light quantity of the photo detector element and reduce an error of a measured value.

Further, a quantity of light from the wide-band light source relative to a wavelength has a wavelength characteristic opposite or substantially opposite from the light from the sample. Thus by combining the light quantity distribution of the light source relative to a detected wavelength and the wavelength characteristics of a sample, it is possible to generate a wavelength band with a constant change or a small change in the wavelength characteristics. Therefore, even when the light quantity distribution of the light source is changed by factors such as a temperature change and a current change, it is possible to minimize a change in the received light quantity of the photo detector element and reduce an error of a measured value, thereby improving the reliability of the analyzing device.

According to the analyzing method and the analyzing device of the present invention, it is possible to reduce a measurement error caused by the dependence of the optical filter on an incident angle and improve the accuracy of measurement and reliability during the analysis of the sample.

According to the analyzing method and the analyzing device of the present invention, it is possible to reduce a measurement error caused by variations in the concentration of the sample, thereby improving the accuracy of measurement and reliability.

BEST MODE FOR CARRYING OUT THE INVENTION (First and Second Embodiments)

An analyzing device according to first and second embodiments of the present invention will be specifically described below in accordance with the accompanying drawings.

Figure 1:
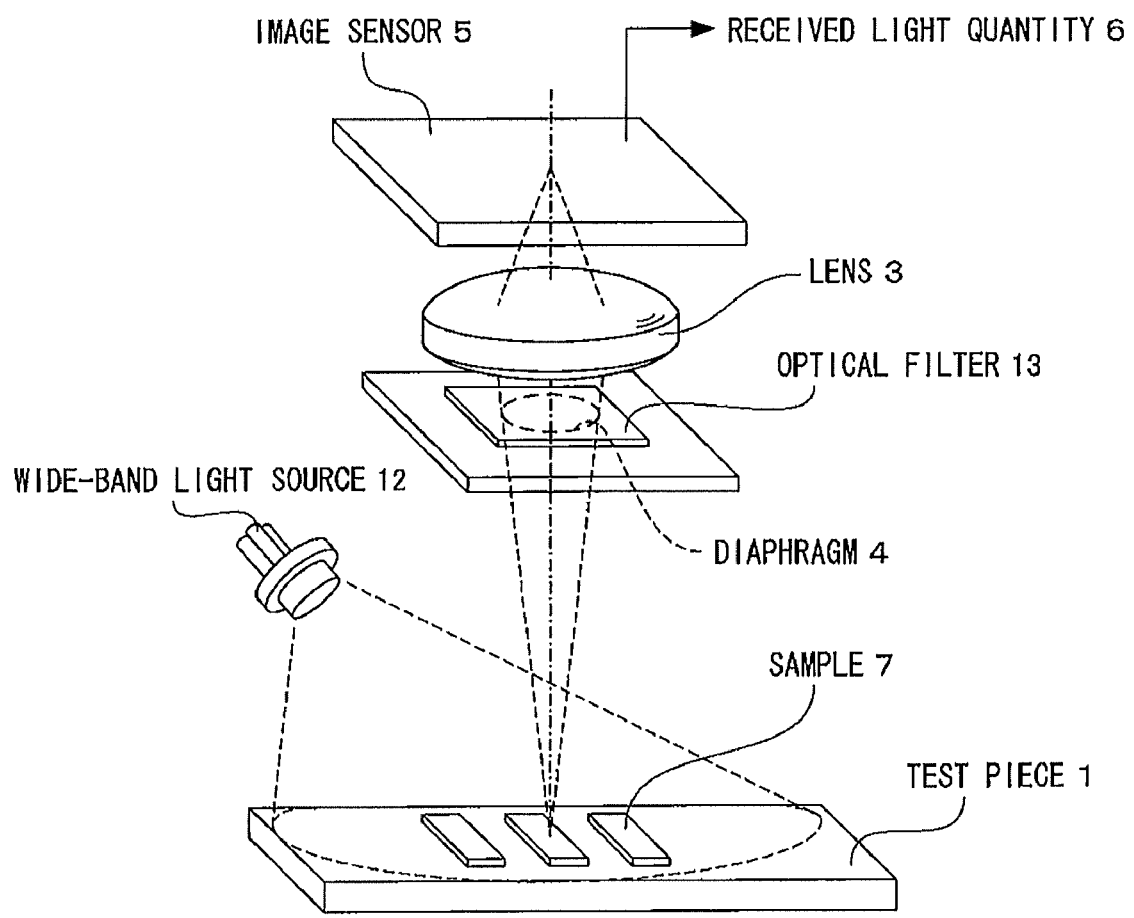
FIG. 1 is a perspective view schematically showing the configuration of an analyzing device according to first and second embodiments of the present invention.
Figure 21:
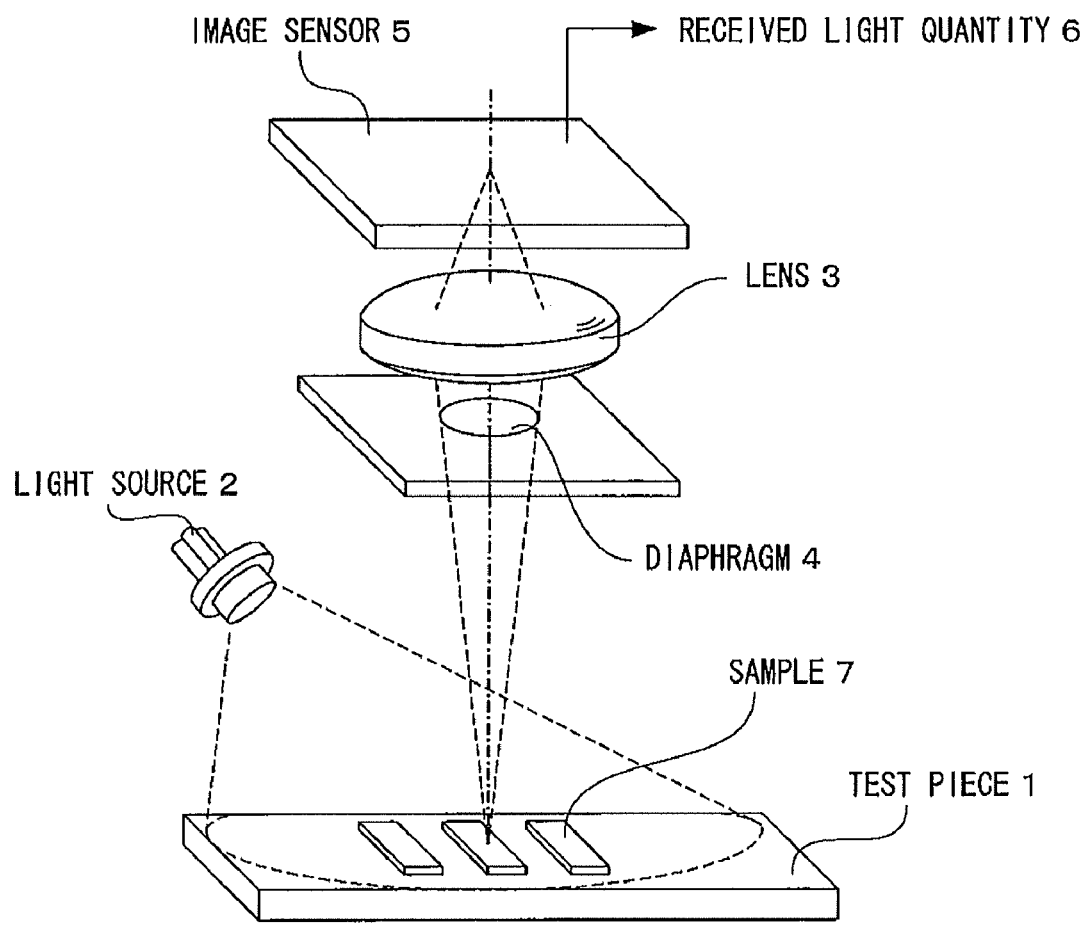
FIG. 21 is a perspective view schematically showing the configuration of an analyzing device of the prior art.
Figure 22A:
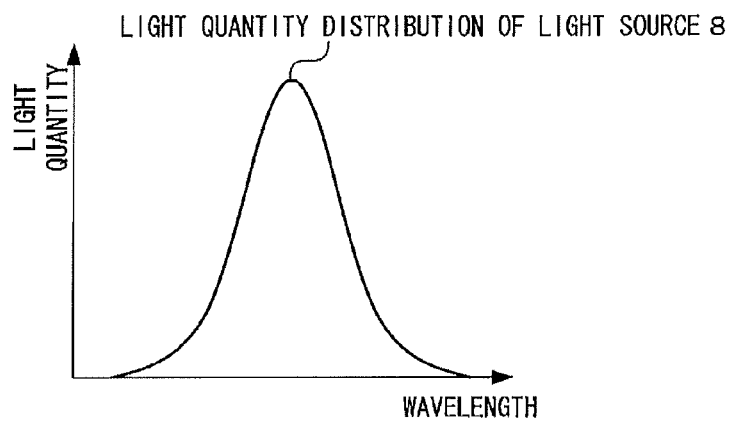
FIG. 22A shows the wavelength characteristics of a narrow-range light source in the analyzing device of the prior art.
Figure 22B:
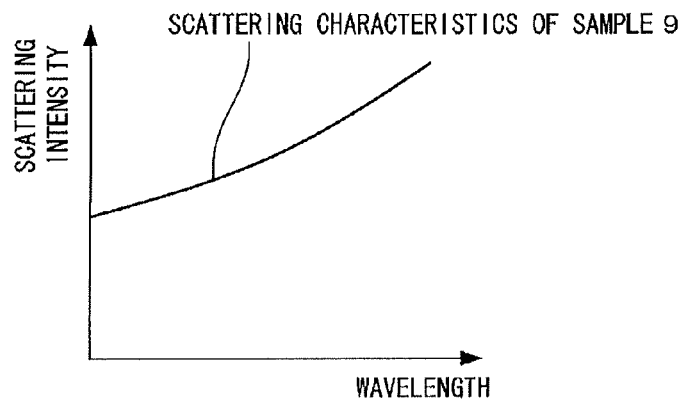
FIG. 22B shows the scattering characteristics of a sample in the analyzing device of the prior art.
Figure 22C:
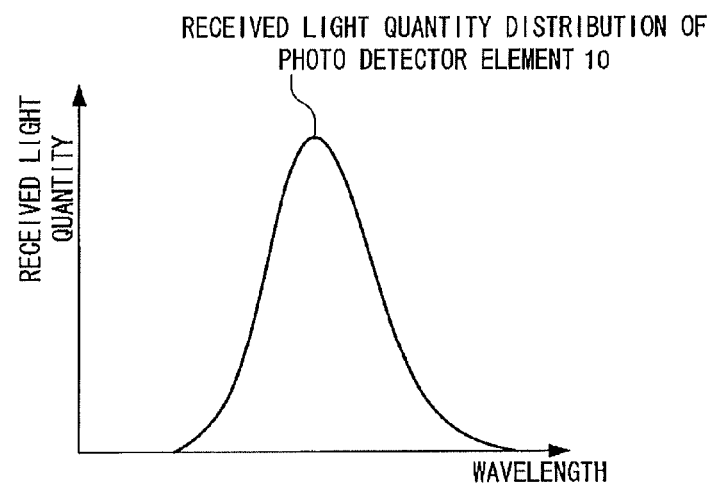
FIG. 22C shows the wavelength characteristics of the received light quantity of a photo detector element in the analyzing device of the prior art.

FIG. 1 schematically shows the configuration of the analyzing device according to the first and second embodiments of the present invention. The configuration of the analyzing device is roughly identical to that of the analyzing device of the prior art shown in FIG. 21 (the same constituent elements are indicated by the same reference numerals and the explanation thereof is omitted). The analyzing device is different from that of the prior art in two points such that a light source is a wide-band light source 12 having a large light quantity distribution relative to a wavelength and an optical filter 13 is provided.

In the first and second embodiments, the optical filter 13 is inserted between a sample 7 and an image sensor 5 acting as a photo detector element (specifically, between a diaphragm 4 and a lens 3 in the first and second embodiments). The wide-band light source 12 has a wide band that satisfactorily enables light emission at a wavelength of at least a band to be detected, even when the temperature or current value of the wide-band light source 12 fluctuates.

Figure 2A:
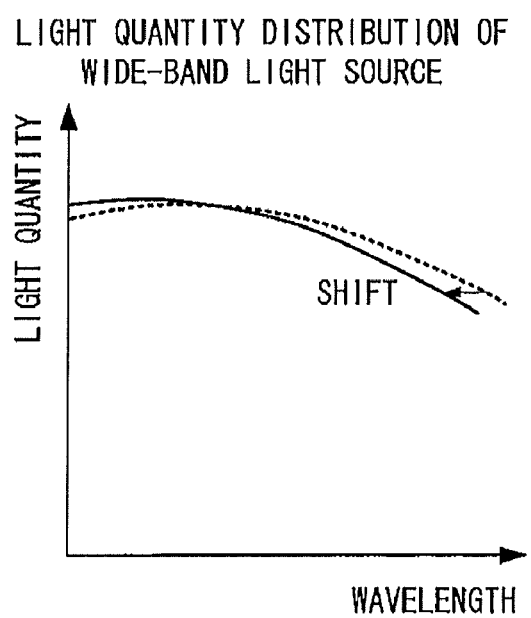
FIG. 2A shows the wavelength characteristics of a wideband light source of the analyzing device according to the first embodiment.
Figure 2B:
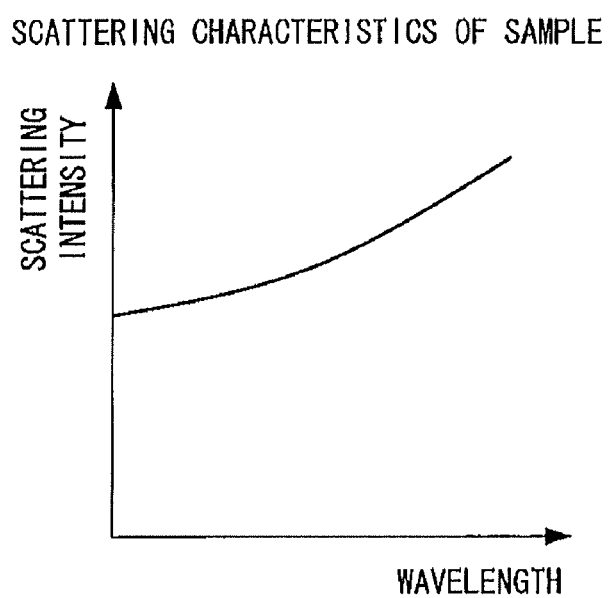
FIG. 2B shows the scattering characteristics of a sample of the analyzing device according to the first embodiment.
Figure 2C:
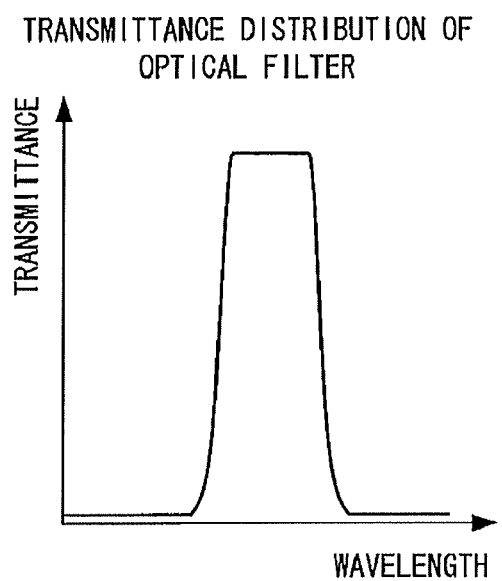
FIG. 2C shows the transmission wavelength characteristics of an optical filter of the analyzing device according to the first embodiment.

The following will describe the wavelength characteristics of the wide-band light source 12, the sample 7, and the optical filter 13. FIGS. 2A to 2C show the wavelength characteristics of the wide-band light source 12, the sample 7, and the optical filter 13, respectively. FIG. 2A shows the light quantity distribution of the wide-band light source 12. For example, the wide-band light source 12 is a wide-range LED featuring a half-width of 130 nm and a peak wavelength of 570 nm. For example, when the temperature or current amount increases, the wavelength characteristics of such a light source (e.g., an LED) tend to shift (move) from a dotted line to a solid line (that is, to the short wavelength side) regardless of whether the light source is a wide-band light source or a narrow-range light source. FIG. 2A shows that the light quantity distribution of the wide-band light source 12 has been shifted from the dotted line to the solid line by a change in temperature or current amount.

FIG. 2B shows the scattering characteristics of the sample 7 acting as a subject (the scattering characteristics of the sample 7 are received by the image sensor 5). For example, when the sample 7 is red, the scattering intensity increases on the long wavelength side. FIG. 2C shows the transmittance distribution of the optical filter 13. The optical filter 13 is, for example, a band-pass filter capable of limiting a transmission wavelength band. By using the wide-band light source 12, the sample 7, and the optical filter 13 with the wavelength characteristics of FIGS. 2A to 2C, the wavelength characteristics (the characteristics of FIGS. 2A, 2B, and 2C) are combined (hereinafter, this state will be conceptually called (A)×(B)×(C)), so that the image sensor 5 has a received light quantity distribution of FIG. 2D.

It is more desirable to combine the wide-band light source 12 and the sample 7 with the wavelength characteristics of FIGS. 2A and 2B such that the wavelength characteristics are combined ((A)×(B)) as flat as possible. For example, when the sample 7 has scattering characteristics increasing with wavelength, the wide-band light source 12 is selected so as to have characteristics decreasing with wavelength. Thus the combined wavelength characteristics (conceptually the wavelength characteristics of (A)×(B)) substantially become flat. In this way, by using the wide-band light source 12 whose wavelength characteristics are reversed or substantially reversed from light from the sample 7 relative to a wavelength, the combined wavelength characteristics ((A)×(B)) substantially become flat. The optical filter 13 is used for selecting a wavelength band in which the wavelength characteristics ((A)×(B)) of the combined wide-band light source 12 and sample 7 are flat. The wavelength band desirably allows the wavelength characteristics (A)×(B) to become flat or less steep. When a wavelength band is selected such that the wavelength characteristics of the combined wide-band light source 12 and sample 7 (that is, conceptually the wavelength characteristics of (A)×(B)) are not flat, the optical filter 13 desirably has a narrow band, thereby suppressing variations in wavelength characteristics at a wavelength having passed through the optical filter 13.

Figure 2D:
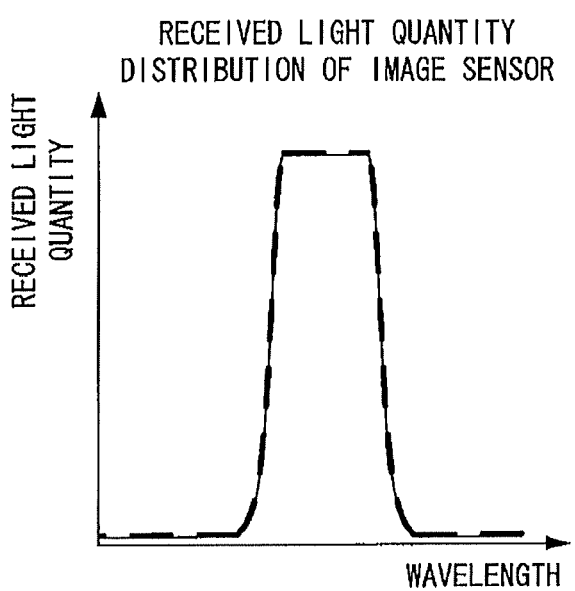
FIG. 2D shows the wavelength characteristics of the received light quantity of an image sensor of the analyzing device according to the first embodiment.
Figure 23A:
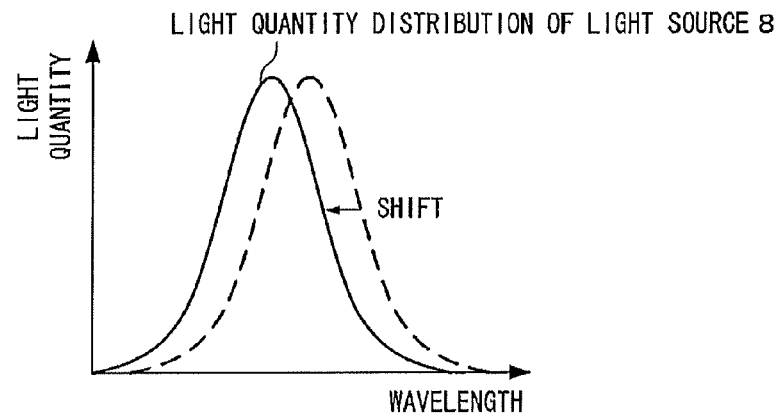
FIG. 23A shows wavelength characteristics when the light quantity distribution of the narrow-range light source is changed in the analyzing device of the prior art.
Figure 23B:
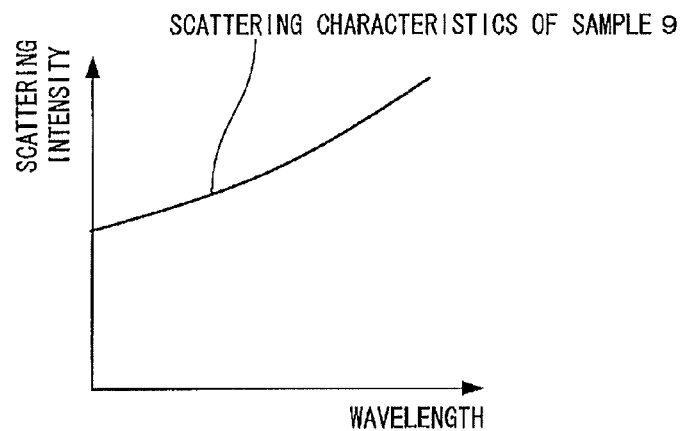
FIG. 23B shows the scattering characteristics of the sample in the analyzing device of the prior art.
Figure 23C:
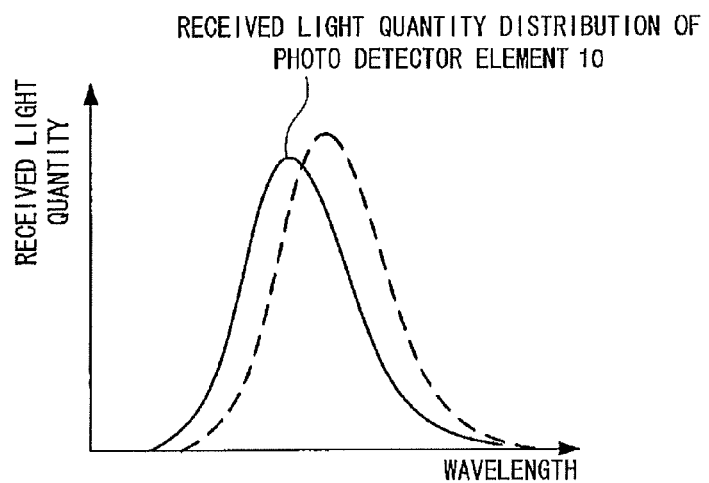
FIG. 23C shows the wavelength characteristics of the received light quantity of the photo detector element when the light quantity distribution of the narrow-range light source is changed in the analyzing device of the prior art.

With this configuration, even in the case where the light quantity distribution of the wide-band light source 12 is shifted from the dotted line to the solid line of FIG. 2A by factors such as a temperature change and a current change, a change of the combined wide-band light source 12 and sample 7 relative to a wavelength (that is, conceptually the wavelength characteristics of (A)×(B)) is smaller than that of a narrow-range light source (see FIGS. 23A to 23C). Further, the optical filter 13 limits the transmission band, thereby further reducing a change in the received light quantity of the image sensor 5 as shown in FIG. 2D (a shift from the dotted line to the solid line), that is, a measurement error.

Figure 3A:
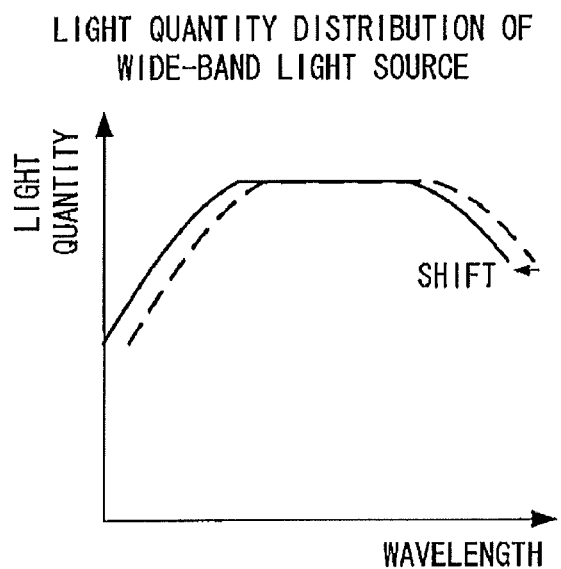
FIG. 3A shows the wavelength characteristics of a wideband light source of the analyzing device according to the second embodiment of the present invention.
Figure 3B:
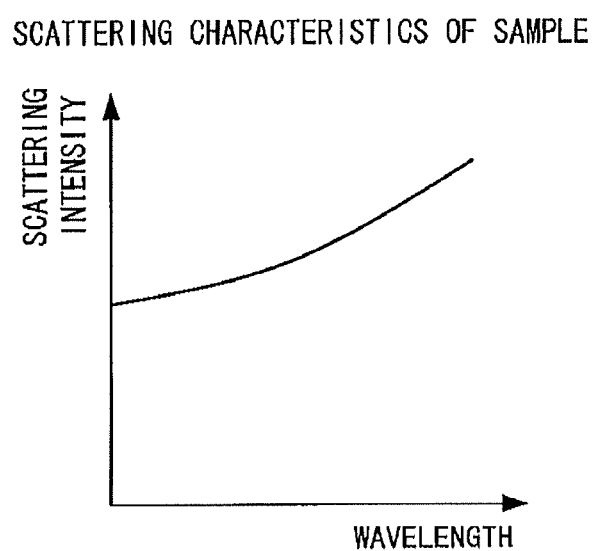
FIG. 3B shows the scattering characteristics of a sample of the analyzing device according to the second embodiment.
Figure 3C:
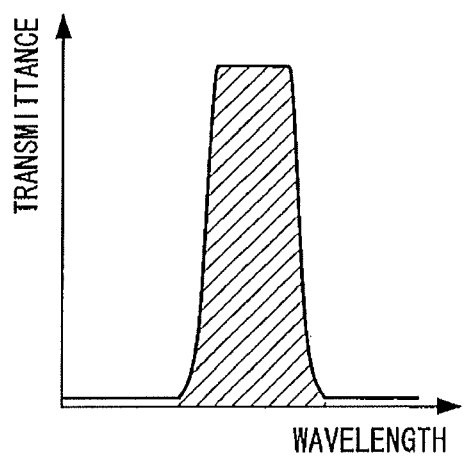
FIG. 3C shows the transmission wavelength characteristics of an optical filter of the analyzing device according to the second embodiment.
Figure 3D:
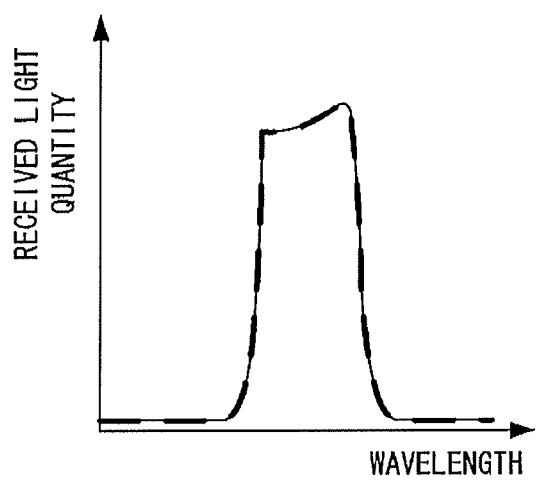
FIG. 3D shows the wavelength characteristics of the received light quantity of an image sensor of the analyzing device according to the second embodiment.

As shown in FIG. 3A, the wide-band light source 12 may have flat or substantially flat characteristics around the transmission band of the optical filter 13 (Second Embodiment). The wide-band light source 12 having such characteristics does not change or hardly changes in light quantity in the transmission band of the optical filter 13 in FIG. 3C (a shaded area in FIG. 3C) even in the case of a wavelength shift. Thus as shown in FIG. 3D, a change in received light quantity naturally becomes small.

The effect of the configuration of the present invention will be discussed below. For example, considering a measurement error of absorbance that has been widely used as an index for measuring the concentration of a subject (sample 7) through light, in the prior art configuration, the narrow-range light source 2 (see FIGS. 23A to 23C) having a wavelength shift of −6 nm causes a measurement error of at least 5% on the sample 7. The narrow-range light source 2 is, for example, an LED light source having a peak wavelength of 610 nm and a half-width of 15 nm. In the configuration of the present invention, however, the optical filter 13 having a transmission band of, e.g., 600 nm to 625 nm can suppress a measurement error to 0.1% or less on the sample 7 even when the wavelength of the wide-band light source 12 is shifted by −6 nm. The measurement error can be further reduced by narrowing the transmission band of the optical filter 13. Thus it is possible to considerably reduce a measurement error and improve reliability.

In the first and second embodiments, the image sensor 5 is used as a photo detector element. The photo detector element is not particularly limited and thus a light receiving element such as a photodiode may be used as a photo detector element.

(Third Embodiment)

An analyzing method and an analyzing device according to a third embodiment of the present invention will be specifically described below in accordance with the accompanying drawings.

Referring to FIGS. 24 to 27C, the following will discuss an analyzing device and an analyzing method of a comparative example (comparative example 1) prior to the explanation of the analyzing method and the analyzing device according to the third embodiment of the present invention.

Figure 24:
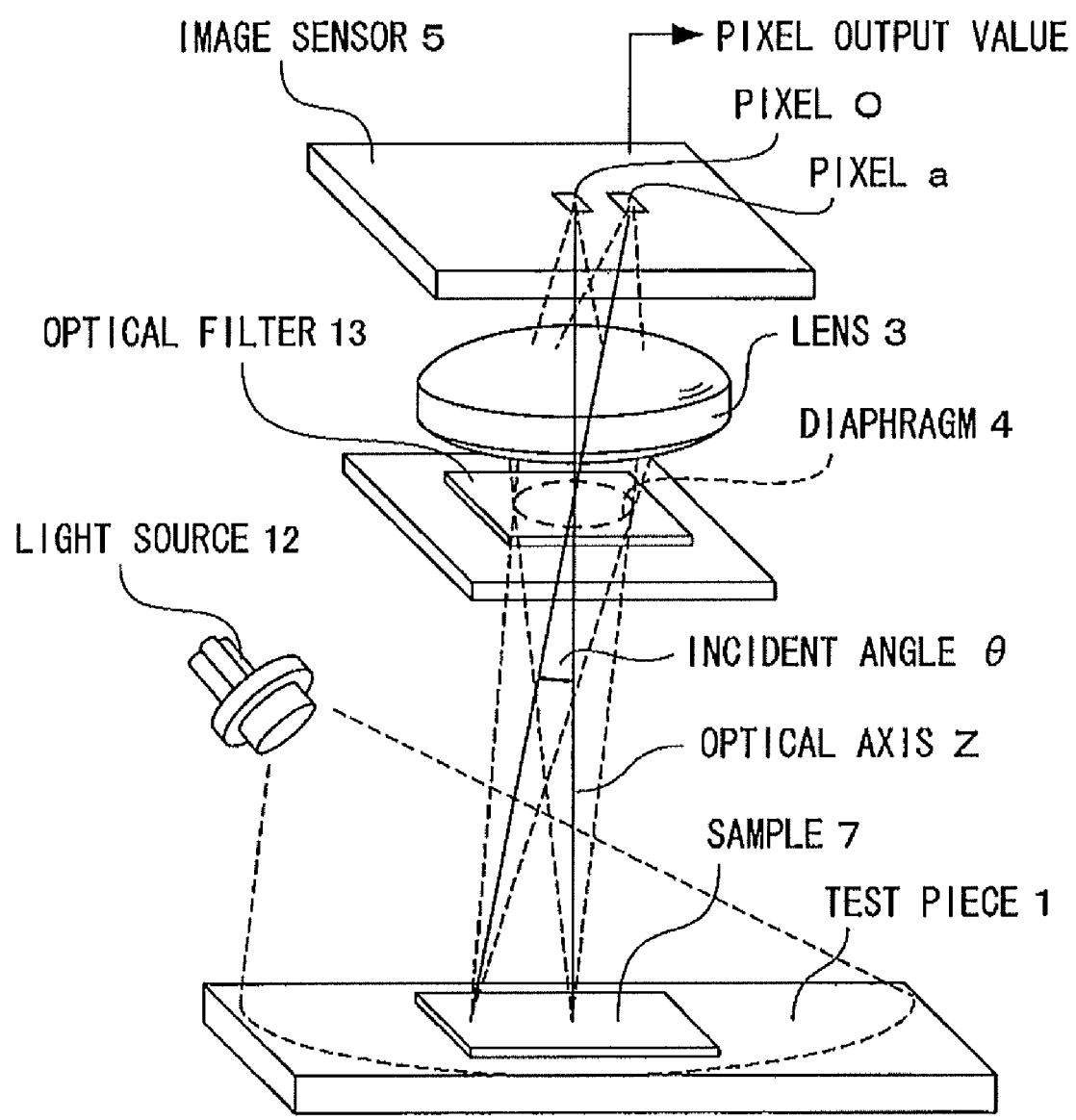
FIG. 24 is a perspective view schematically showing the configuration of an analyzing device according to a comparative example (comparative example 1) of the third embodiment.

As shown in FIG. 24, in this analyzing device, light from a light source (wide-band light source) 12 is emitted to a test piece 1 on which a sample 7 is set, scattered light (may be transmitted light or reflected light) from the test piece 1 is passed through an optical system made up of a lens 3, a diaphragm 4, an optical filter 13, and so on and is emitted to an image sensor 5 that is made up of a CCD and the like, and an image is formed on the image sensor 5. A quantity of light obtained on each pixel of the image sensor 5 (in FIG. 24, pixel O is located on optical axis Z that is the central axis of the optical system and pixel a is not located on the optical axis) is converted to a pixel output value and the pixel output value is analyzed, so that the concentration of the sample 7 set on the test piece 1 is quantified.

In order to determine the concentration of the sample 7 set on the test piece 1 in the analyzing device configured thus, it is necessary to obtain light (a quantity of scattered light, transmitted light, or reflected light) from the sample 7 through the pixel of the image sensor 5. In the wavelength characteristics of the light source 12, the sample 7, and the image sensor 5, the pixel output value of the image sensor 5 is obtained as an integral satisfying the transmission wavelength band of the optical filter 13, out of wavelength characteristics obtained from the product of the quantity of light from the light source 12, the scattering intensity of the sample 7, and the sensitivity of the image sensor 5.

Figure 25A:
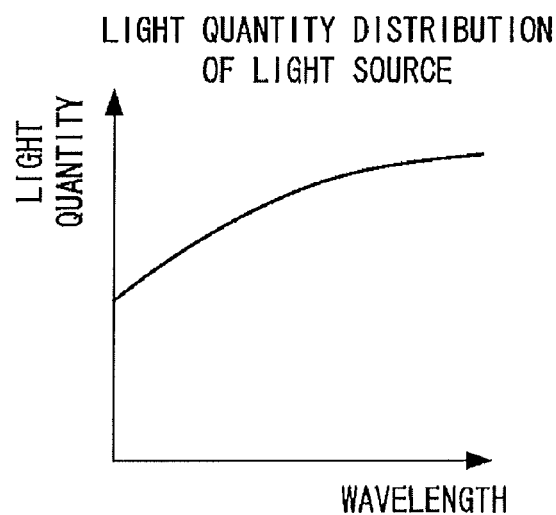
FIG. 25A shows the wavelength characteristics of a light source of the analyzing device.
Figure 25B:
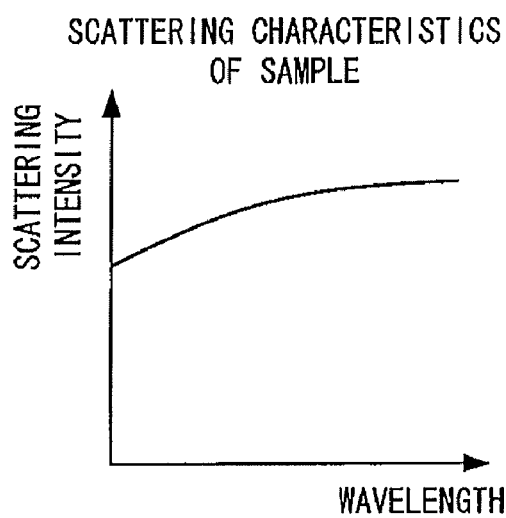
FIG. 25B shows the scattering characteristics of a sample of the analyzing device.
Figure 25C:
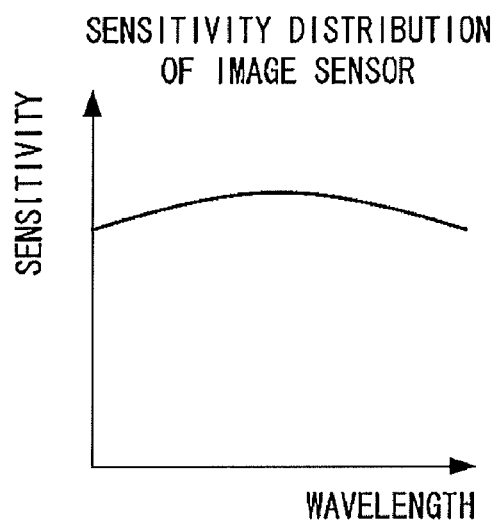
FIG. 25C shows the sensitivity distribution of an image sensor of the analyzing device.
Figure 25D:
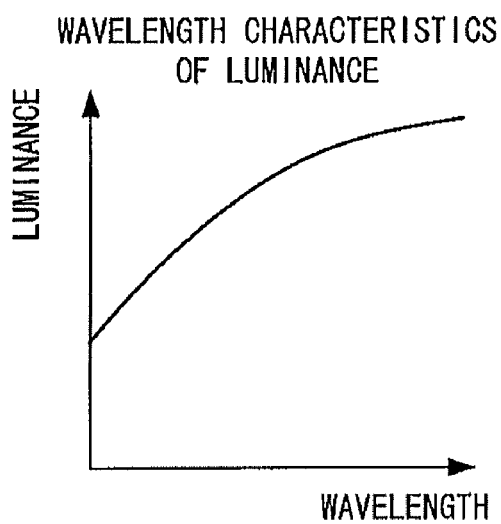
FIG. 25D shows the wavelength characteristics of luminance in the analyzing device.
Figure 26A:
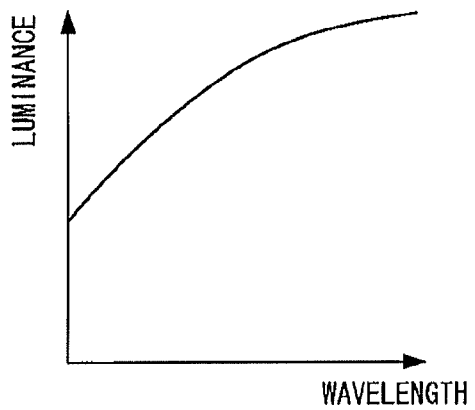
FIG. 26A shows the wavelength characteristics of luminance in the analyzing device.
Figure 26B:
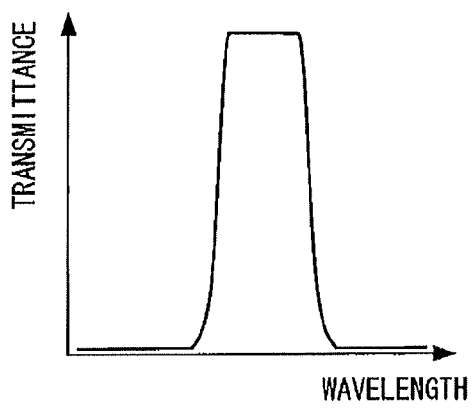
FIG. 26B shows the transmission characteristics of an optical filter in the analyzing device.
Figure 26C:
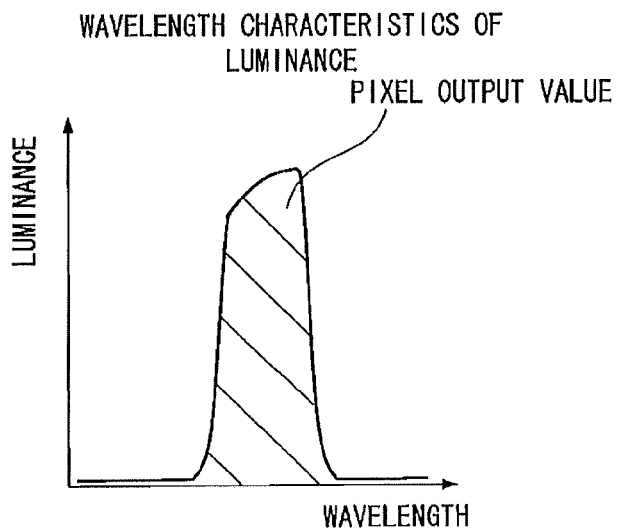
FIG. 26C shows the wavelength characteristics of luminance after passage through the optical filter in the analyzing device.

For example, as shown in FIGS. 25A to 25D and 26A to 26C, in the case where the light source 12 has a light quantity distribution relative to a wavelength as shown in FIG. 25A, the sample 7 has scattering characteristics as shown in FIG. 25B, and the image sensor 5 has a sensitivity distribution as shown in FIG. 25C, the wavelength characteristics of luminance are obtained as shown in FIG. 25D. Further, as to wavelengths characteristics shown in FIG. 26A (identical to the characteristics of FIG. 25D), a wavelength is limited by the optical filter 13 having the transmission characteristics of FIG. 26B, so that as shown in FIG. 26C, wavelength characteristics indicating luminance after passage through the optical filter 13 are obtained. The integral of the wavelength characteristics (a shaded area in FIG. 26C) is the pixel output value of the image sensor 5.

Figure 27A:
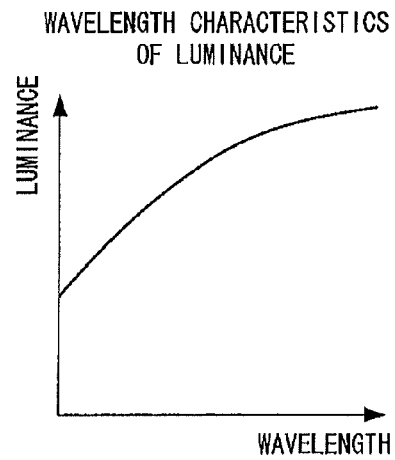
FIG. 27A shows the wavelength characteristics of luminance in the analyzing device.
Figure 27B:
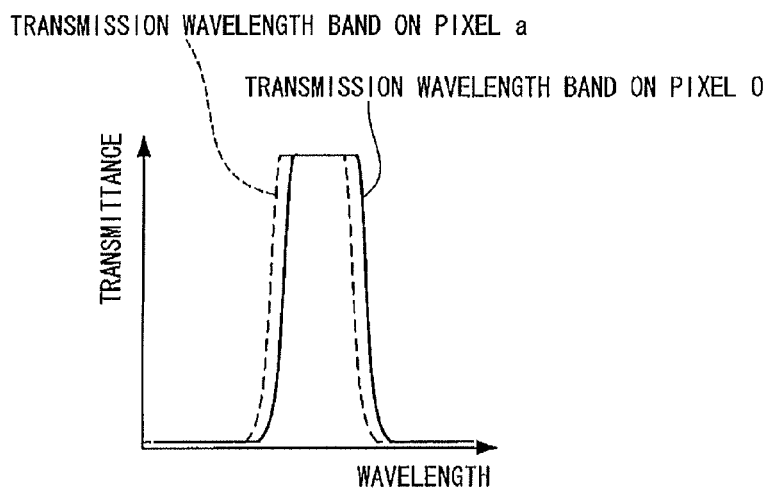
FIG. 27B shows the transmission characteristics of the optical filter in the analyzing device.
Figure 27C:
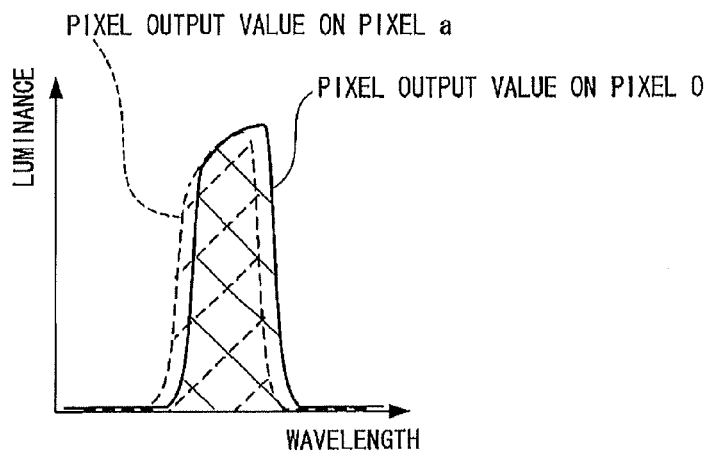
FIG. 27C shows the wavelength characteristics of luminance after passage through the optical filter in the analyzing device.

As shown in FIG. 24, when light (scattered light) from the sample 7 is emitted on the optical axis Z, the light is substantially perpendicular to the optical filter 13 (that is, along the optical axis Z) and forms an image on the pixel O. When scattered light from the sample 7 forms an image on the pixel a, the light has been separated from the optical axis Z and forms an incident angle θ relative to a perpendicular line (optical axis z) that is orthogonal to the optical filter 13. In this case, the optical filter 13 has a transmission wavelength band that shifts in a negative direction according to the light incident angle θ, that is, the optical filter 13 is dependent on an incident angle. Thus as indicated by dotted lines in FIG. 27B, the wavelength band of the light forming an image on the pixel a is shifted in the negative direction relative to the pixel O. Consequently, also in the wavelength characteristics of luminance on the pixel a in FIG. 27C, the wavelength band is shifted in the negative direction. Further, when the luminance changes relative to a wavelength as shown in FIG. 27A, the pixel output value of the pixel a also fluctuates (decreases in FIGS. 27A to 27C) with the luminance change. In other words, even when the same quantity of light is obtained from the same sample 7, the pixel output value varies among pixel positions in the image sensor 5, causing a measurement error.

The analyzing device and the analyzing method according to the third embodiment of the present have been devised to address this problem.

Figure 4:
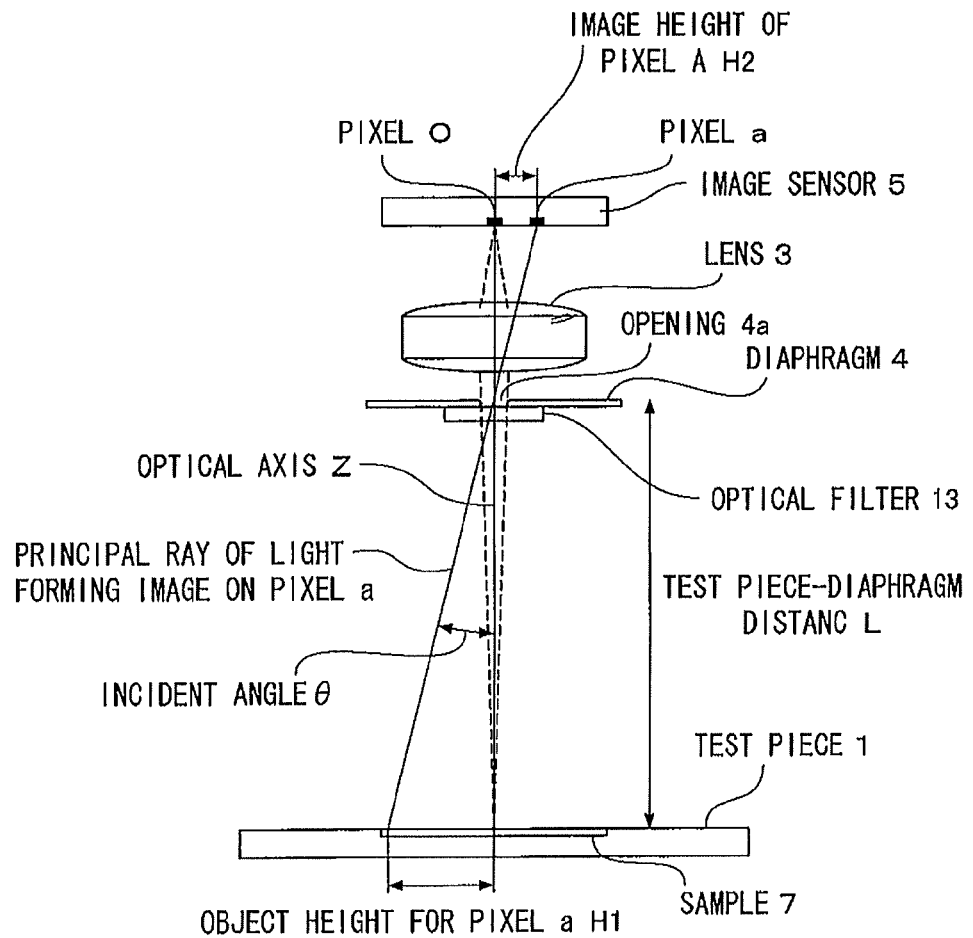
FIG. 4 is a front view schematically showing the configuration of an analyzing device according to a third embodiment of the present invention.

FIG. 4 is a front view schematically showing the configuration of the analyzing device according to the third embodiment of the present invention. The configuration of FIG. 4 is roughly identical to the configuration of the analyzing device of the prior art shown in FIG. 24. The same constituent elements are indicated by the same reference numerals and the explanation thereof is omitted. As in the analyzing device of the prior art, the analyzing device has a light source for irradiating a test piece 1 with light (the light source is similar to the wide-band light source 12 of FIG. 1) but the light source is omitted in FIG. 4.

The analyzing device according to the third embodiment of the present invention is different from the analyzing device of FIGS. 24 to 27C in that a control unit (not shown) is provided for executing an original correction algorithm for correcting pixel output values from the pixels of an image sensor 5. The control unit for executing the correction algorithm includes: a filter incident angle detector that detects a filter incident angle of light incident on an optical filter 13, the light forming an image on the pixel; a shift amount obtaining unit that obtains a shift amount (movement) of the filter band of the optical filter 13 according to the filter incident angle; a correction coefficient setting unit that sets a correction coefficient according to the shift amount; a correcting unit that corrects a luminance value by using the correction coefficient; and a concentration obtaining unit that obtains the concentration information of a sample based on the corrected luminance value.

The following will specifically describe the correction algorithm.

First, an incident angle is detected when light from a sample 7 passes through the optical filter 13. FIG. 4 shows an optical path in an optical system made up of a lens 3, a diaphragm 4, the optical filter 13, and so on. In FIG. 4, optical axis Z of the optical system is the principal ray of light incident on the optical filter 13 at right angles, that is, the principal ray of light forming an angle of 0° relative to a perpendicular line crossing the optical filter 13, and light having passed on the optical axis Z from the sample 7 forms an image on pixel O. The light forming an image on the pixel O is made up of an infinite number of rays distributed in a conical shape, and an opening 4*a* of the diaphragm 4 is formed at the bottom of the conical shape. Thus rays other than the optical axis form certain incident angles on the optical filter 13 (an angle of inclination relative to the optical axis Z). It is assumed that a diaphragm is sufficiently small in diameter, that is, all the rays are close to the single optical axis Z. In this case, the transmission band of the optical filter 13 corresponds to the pixel O and conforms to a set value without depending on an incident angle. Thus the pixel output value obtained on the pixel O is a true value.

In the case of light forming an image on pixel a with dependence on an incident angle on the optical filter 13, when it is assumed that all the rays are close to the principal ray of light as on the pixel O, an incident angle θ is formed as expressed in (Equation 1):

$$\theta = \tan^{-1}(H1/L) \quad \text{(Equation 1)}$$

where L is a distance between the test piece 1 and the diaphragm 4 (test piece-diaphragm distance) and H1 is an object height for the pixel a (a distance between the position of the optical axis and a part of the sample 7 on the test piece 1, the part corresponding to the pixel a).

The object height H1 for the pixel a can be determined by an image height (a distance between the pixel a and the center of the image sensor 5, the center corresponding to the optical axis Z) H2 of the pixel a and an image magnification b of the optical system as expressed in (Equation 2):

$$H1 = H2/b \quad \text{(Equation 2)}$$

According to (Equation 1) and (Equation 2), it is possible to determine the incident angle θ of light forming an image on the pixel a.

Figure 5:
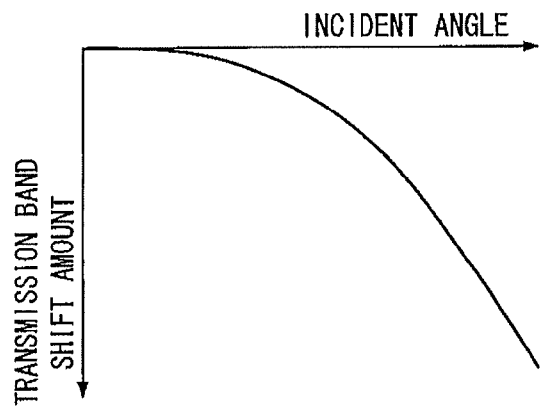
FIG. 5 shows the relationship (characteristics) between an incident angle on an optical filter and a transmission band shift amount in the analyzing device and an analyzing method according to the third embodiment.

Next, a transmission band shift (transmission band movement) caused by the dependence of the optical filter 13 on an angle is determined. The incident angle θ on the optical filter 13 and a transmission band shift corresponding to the incident angle θ have been determined as specifications of the optical filter 13. For example, the incident angle θ and the transmission band shift can be easily obtained as design data during the fabrication of the optical filter 13 or by measurement after the optical filter is obtained. The relationship between the incident angle θ on the optical filter 13 and the transmission band shift forms, for example, a declining curve as shown in FIG. 5. A feature of the relationship is that the transmission band shifts in the negative direction as the incident angle on the optical filter 13 increases. This graph indicates the wavelength band of light forming an image on the pixel a.

Figure 6:
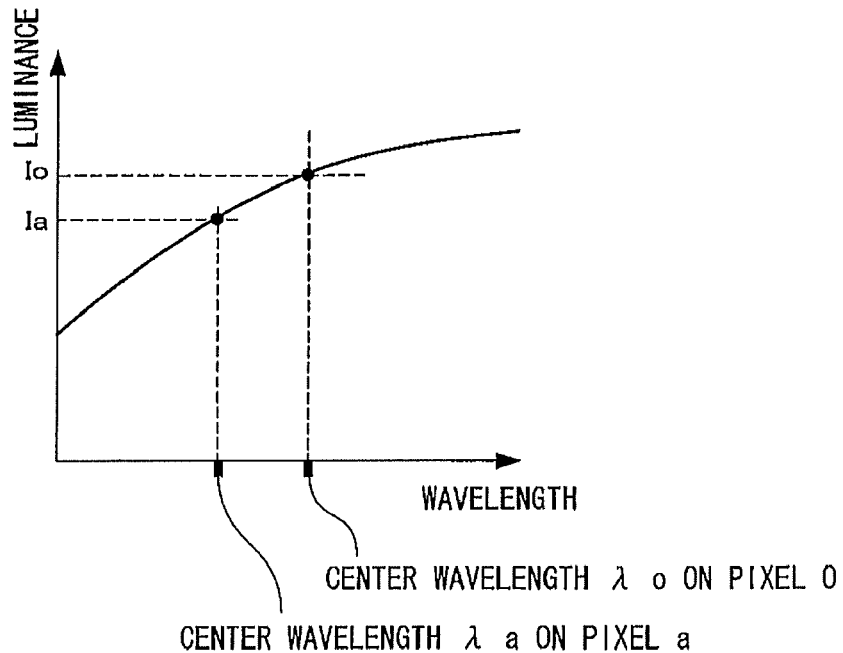
FIG. 6 shows the wavelength characteristics of luminance in the analyzing device and the analyzing method according to the third embodiment.

Referring to FIG. 6, the following will describe a method of obtaining a correction coefficient according to a transmission band shift. The graph of FIG. 6 shows the wavelength characteristics of luminance in FIG. 25D. The characteristics show a change of measurement error caused by the dependence of the optical filter 13 on an incident angle. Thus the correction efficient is determined by the graph.

First, it is assumed that the wavelength band of light forming an image on the pixel O has a center wavelength of λo, which is the set value of the transmission band of the optical filter 13 as previously mentioned. Assuming that the wavelength band of light forming an image on the pixel a has a center wavelength of λa, the value of λa can be determined by an incident angle and a transmission band shift. Luminance Io and luminance Ia at the center wavelength λo and the center wavelength λa can be determined by this graph. In other words, luminance to be determined as the luminance Io on the pixel a is obtained as the luminance Ia because of a transmission band shift resulting from the dependence of the optical filter 13 on an angle. In order to correct the luminance Ia to Io, it is necessary to multiply the luminance Ia by a correction coefficient. A correction coefficient αa is determined as follows:

$$\alpha a = Io/Ia \quad \text{(Equation 3)}$$

Finally, referring to FIG. 7, a correction method using the correction coefficient will be described below.

Figure 7:
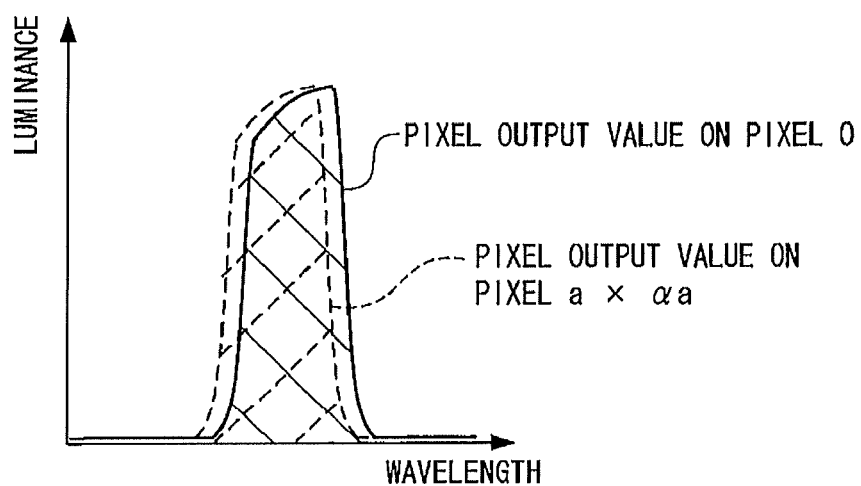
FIG. 7 shows the wavelength characteristics of luminance after passage through the optical filter in the analyzing device and the analyzing method according to the third embodiment.

As shown in FIG. 7, a pixel output value on the pixel a affected by the dependence of the optical filter 13 on an incident angle is multiplied by the correction coefficient αa. Thus luminance at each wavelength is increased by the multiplication of the correction coefficient αa up to a level as high as the luminance of the pixel O. In other words, the pixel output value on the pixel a is the integrated value of luminance relative to a wavelength and comes close to the pixel output value on the pixel O, that is, the true value, so that the influence of the dependence of the optical filter 13 on an incident angle is corrected and is substantially eliminated. Also on the other pixels on the image sensor 5, correction coefficients are calculated by the same process and obtained pixel output values are multiplied by the correction coefficients corresponding to the respective pixel positions, thereby minimizing the influence of the dependence of the optical filter 13 on an incident angle.

For example, when the wavelength characteristics of the sample 7 do not vary with time or environment, the wavelength characteristics of luminance also remain the same. Thus only a single pattern of correction coefficient may be shared by the pixels. When several samples 7 are used, correction coefficients corresponding to the wavelength characteristics of the respective samples 7 may be prepared beforehand and a correction coefficient pattern may be changed for each of the samples 7.

As previously mentioned, the algorithm is used in which an incident angle on the optical filter 13 is determined, a shift amount of the transmission band of the optical filter 13 is determined according to the angle, and a correction coefficient determined by a luminance change corresponding to the shift amount is multiplied by the corresponding pixel output value, so that a pixel output value close to a true value can be obtained at any pixel on the image sensor 5.

In this way, the analyzing method and the analyzing device according to the present invention can reduce a measurement error caused by the dependence of the optical filter 13 on an incident angle and improve the accuracy of measurement and reliability during the analysis of the sample 7. For example, when observing a measurement error at absorbance, which has been widely used as an index for measuring the concentration of a subject (sample 7) with light, without making the correction, the sample 7 has a measurement error of at least 5% at an incident angle θ of about 30° on the optical filter 13, whereas the correction using the algorithm can suppress the measurement error of the concentration of the sample 7 to 0.2% to 0.3%.

In the present embodiment, the luminance value is corrected using the correction coefficient and the concentration information of the sample 7 is obtained based on the corrected luminance value. The method of obtaining the concentration information is not particularly limited. Digital data corresponding to the luminance value may be corrected and the concentration information of the sample 7 may be obtained based on the corrected data.

(Fourth Embodiment)

An analyzing device and an analyzing method according to a fourth embodiment of the present invention will be described below.

Referring to FIGS. 28 to 32C, the following will discuss an analyzing device and an analyzing method of a comparative example (comparative example 2) prior to the explanation of the analyzing device and the analyzing method according to the fourth embodiment of the present invention.

Figure 28:
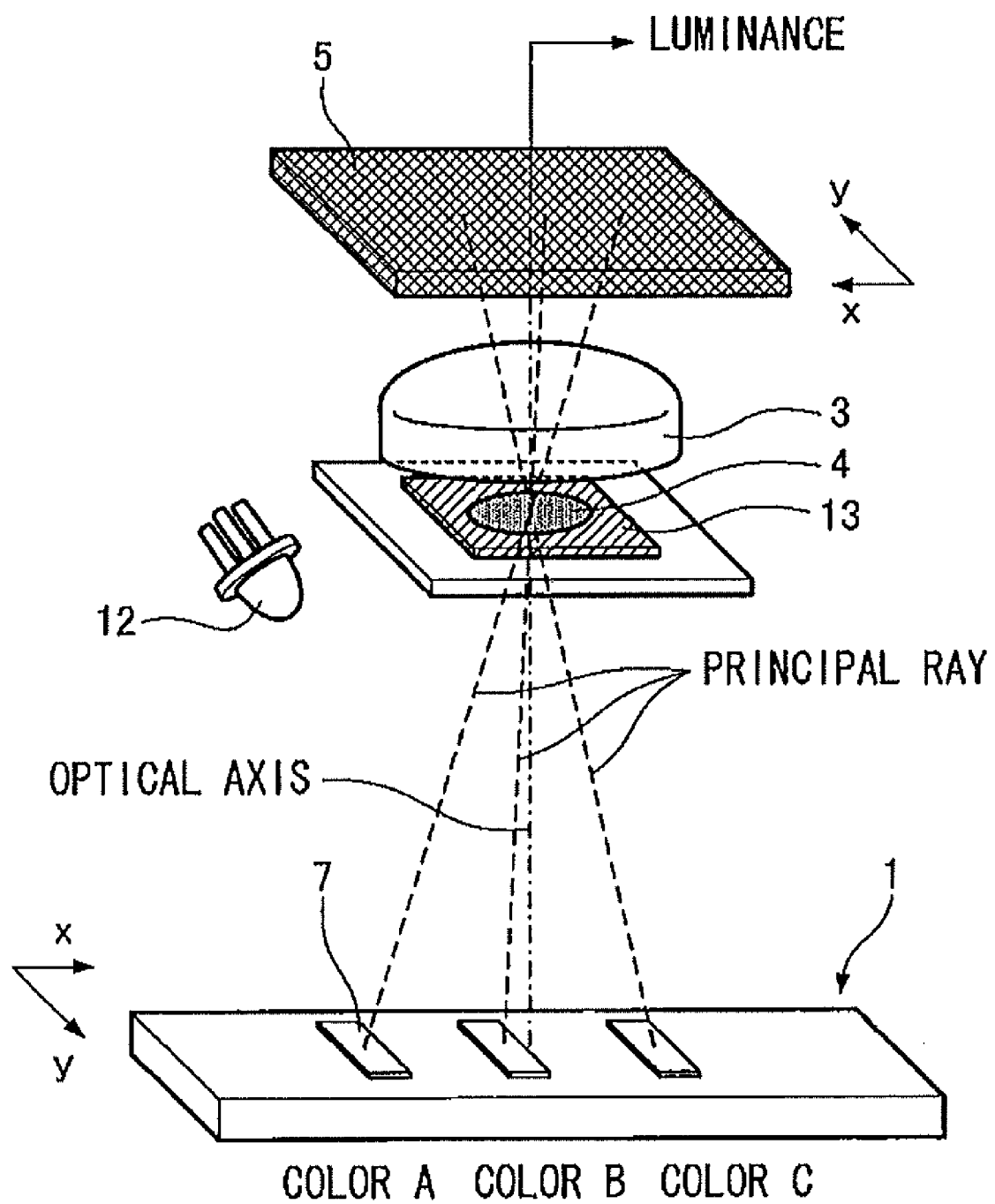
FIG. 28 is a perspective view schematically showing a state in which a test piece is measured by an analyzing device according to a comparative example (comparative example 2) of the fourth embodiment.

As shown in FIG. 28, light from a light source 12 is emitted to a test piece 1 on which samples 7 are set, scattered light (may be transmitted light or reflected light) from the test piece 1 is passed through an optical system made up of a lens 3, a diaphragm 4, an optical filter 13, and so on and is emitted to an image sensor 5 made up of a CCD and the like, and an image is formed on the image sensor 5. A quantity of light obtained on each pixel of the image sensor 5 is converted to the luminance of the pixel and the luminance is analyzed, so that the concentrations of the samples 7 set on the test piece 1 are quantified.

In this analyzing method, when luminance is obtained according to the wavelength characteristics of the sample 7 and the wavelength characteristics of the light source 12, the luminance decreases with a distance from the optical axis because of the dependence of the optical filter 13 on an angle. Thus as shown in FIGS. 29A to 29C, angle dependence correction coefficients (see FIG. 29B) corresponding to calculated color positions are integrated to luminance (see FIG. 29A) at the respective positions of color portions (hereinafter, will be called colors A, B, and C), so that the luminance is corrected (see FIG. 29C).

Figure 29A:
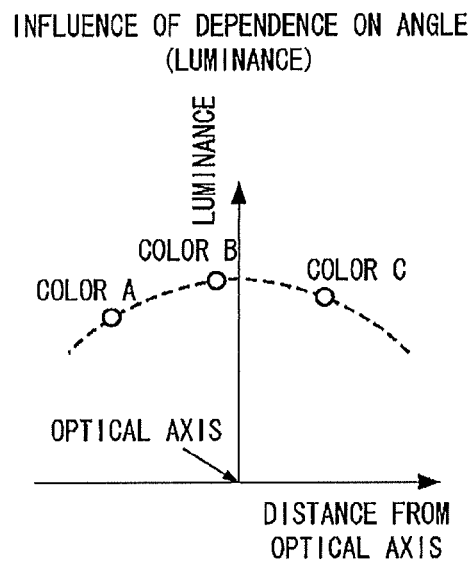
FIG. 29A shows a method of correcting the dependence of an optical filter on an angle according to an analyzing method using the analyzing device of FIG. 28.
Figure 29B:
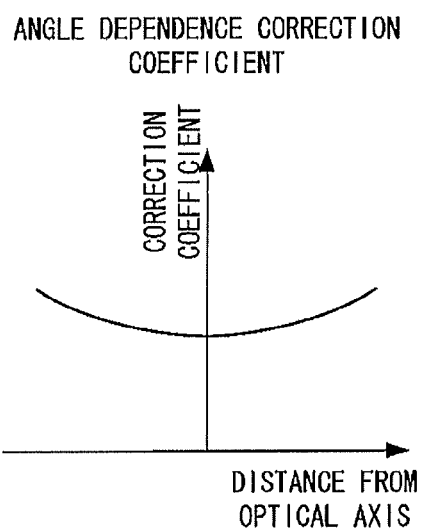
FIG. 29B shows a method of correcting the dependence of the optical filter on an angle according to the analyzing method.
Figure 29C:
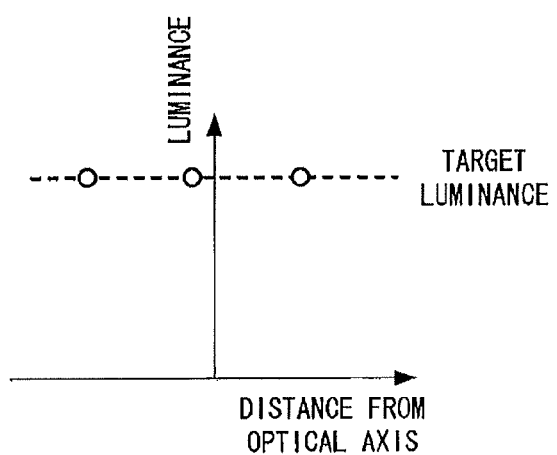
FIG. 29C shows a correction result of the dependence of the optical filter on an angle according to the analyzing method.
Figure 30A:
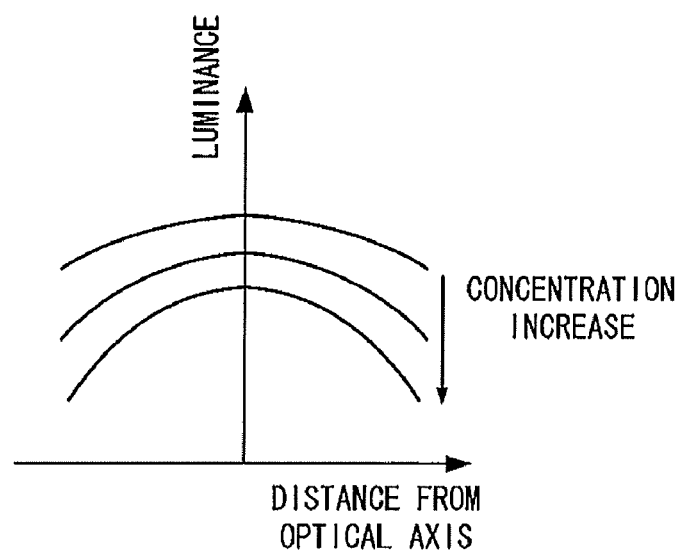
FIG. 30A shows that a rate of change of luminance varies depending on a concentration because of the dependence on an angle according to the analyzing method using the analyzing device of FIG. 28.
Figure 30B:
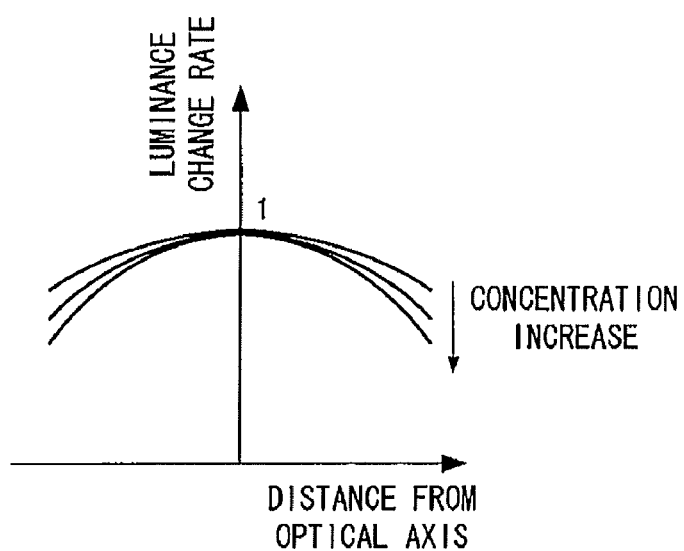
FIG. 30B shows that a rate of change of luminance varies depending on a concentration because of the dependence on an angle according to the analyzing method.

In the analyzing method of FIGS. 29A to 29C, the correction coefficients are derived using the wavelength characteristics of the sample having a certain concentration and then the luminance is corrected. As shown in FIG. 30A, however, a change in luminance relative to a distance from the optical axis increases with the concentration of the sample 7. For example, as shown in FIG. 30B, this characteristic can be easily understood when a luminance distribution at each concentration is normalized at each peak luminance and the rates of change in luminance relative to the peak luminance are compared with one another.

Figure 31:
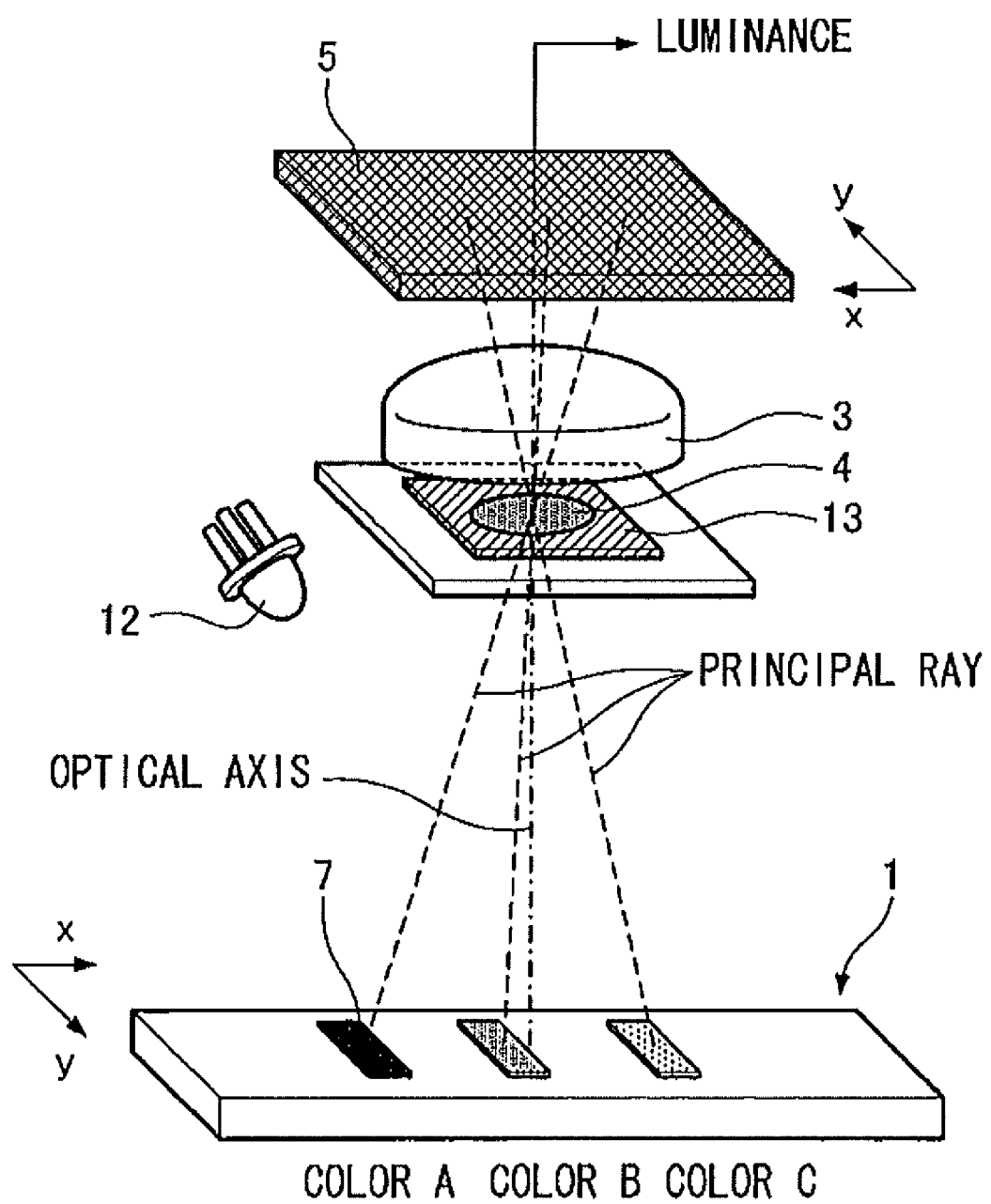
FIG. 31 is a perspective view schematically showing a state in which another test piece is measured by the analyzing device of comparative example 2.
Figure 32A:
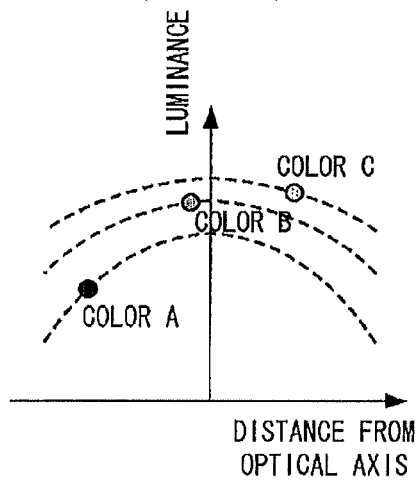
FIG. 32A shows a method of correcting measured portions according to the analyzing method using the analyzing device of FIG. 31.
Figure 32B:
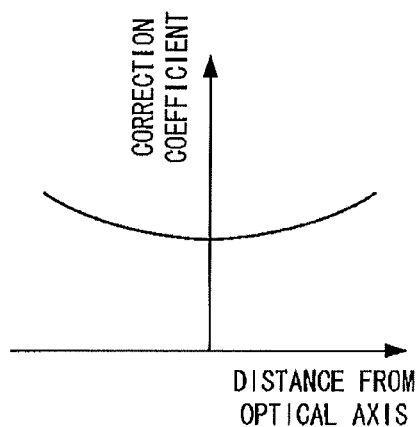
FIG. 32B shows a method of correcting the measured portions according to the analyzing method.
Figure 32C:
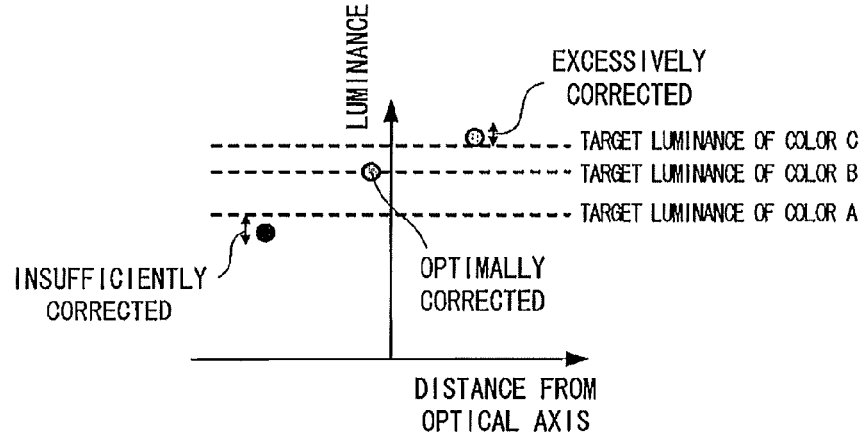
FIG. 32C shows a correction result of the measured portions according to the analyzing method.

However, as shown in FIG. 31, in the case of measurement on the test piece where a sample concentration varies among the color portions (it is assumed that the color A has a high concentration, the color B has a medium concentration, and the color C has a low concentration), when the dependence on an angle is corrected by a correction coefficient that has been determined according to a single concentration on the sample 7 (e.g., the sample concentration of the color B) as shown in FIGS. 32A to 32C, the color A is insufficiently corrected and the color C is excessively corrected, resulting in an error of a measured value.

The analyzing device and the analyzing method according to the fourth embodiment of the present invention have been devised to address this problem.

The configuration of the analyzing device according to the fourth embodiment is substantially identical to that of the analyzing device illustrated in FIG. 28. Thus referring to FIG. 28, the explanation of the analyzing device is omitted. A test piece 1 to be analyzed has the same color portions as in FIG. 28 or 31.

The analyzing device of the fourth embodiment is different from the analyzing device of FIG. 28 in the provision of a control unit (not shown) that executes an original correction algorithm for correcting pixel output values from the pixels of an image sensor 5.

The control unit includes: a luminance calculator that calculates a luminance value beforehand at any position in the image sensor 5 based on the dependence on a filter incident angle and the wavelength characteristics of light from a sample 7 set with various known concentrations on the test piece 1; a first correction coefficient calculator that calculates correction coefficients for matching luminance distributions obtained at the respective concentrations by the luminance calculator with the luminance distribution of any reference concentration selected from the concentrations; a rectilinear approximation unit that makes a rectilinear approximation by plotting the correction coefficients obtained at the respective concentrations by the first correction coefficient calculator, relative to concentration information (e.g., absorbance); a correction function calculator that calculates the correction function of the dependence on a filter incident angle according to the reference concentration, based on the luminance distribution of the reference concentration; a concentration calculator that corrects luminance obtained on the samples 7 separately set to be measured with unknown concentrations on the test piece, by using the correction function obtained by the correction function calculator according to the reference concentration, and calculates the concentration information by using the corrected luminance; a second correction coefficient obtaining unit that obtains the concentration correction coefficients of the samples 7 to be measured, by correlating the concentration information obtained by the concentration calculator with a straight line determined by the rectilinear approximation unit; and a concentration obtaining unit that integrates the concentration correction coefficients obtained by the second correction coefficient obtaining unit to the correction function obtained by the correction function calculator according to the reference concentration, corrects the luminance of the samples 7 to be measured, by using the correction functions after the integration, and obtains again the concentration information of the samples to be measured, by using the corrected luminance.

The following will specifically describe the correction algorithm.

A luminance value at any position in the image sensor 5 is calculated beforehand based on the dependence on a filter incident angle and the wavelength characteristics of light from the samples 7 set with various known concentrations on the test piece 1 that serves as a base (first step).

Figure 8A:
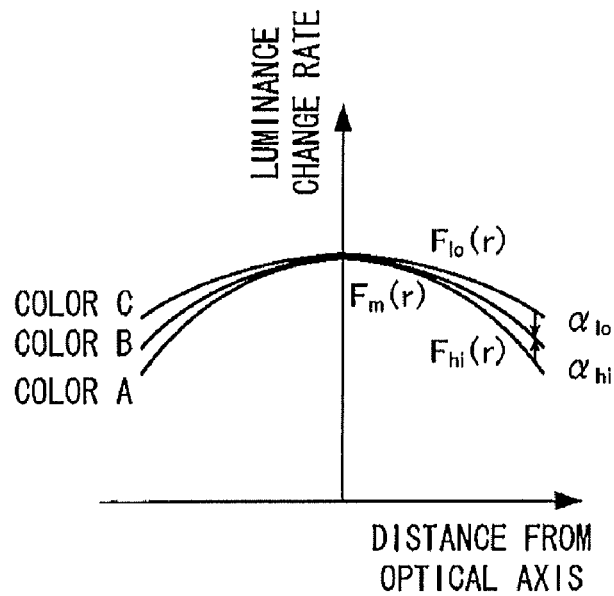
FIG. 8A is an explanatory drawing showing a step of an analyzing method according to a fourth embodiment of the present invention.

FIG. 8A is a graph showing a rate of change of luminance at each concentration of the sample 7. The luminance changes because of the dependence on an angle (correspondence with a distance from the optical axis). As previously mentioned, a rate of change of luminance owing to the dependence on an angle increases with the concentration of the sample 7. A luminance distribution at each concentration of the sample 7 is denoted as function $F(r)$ where $r$ is a distance from the optical axis. The high-concentration sample is denoted as function $F_{hi}(r)$, the medium-concentration sample is denoted as function $F_m(r)$, and the low-concentration sample is denoted as function $F_{lo}(r)$.

Figure 8B:
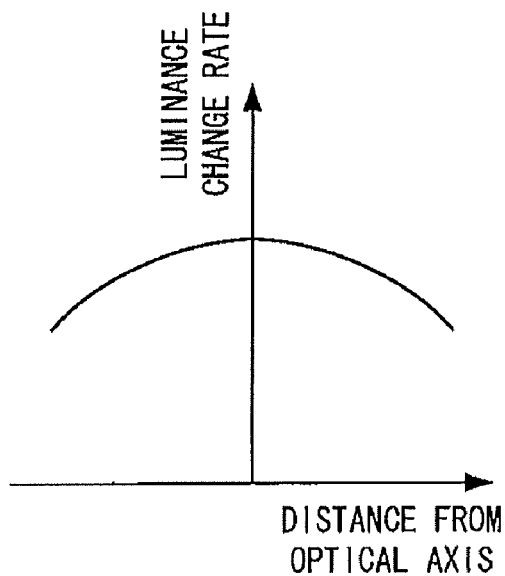
FIG. 8B is an explanatory drawing showing a step of the analyzing method according to the fourth embodiment.

Next, correction coefficients are calculated for matching the luminance distributions obtained at the respective concentrations with the luminance distribution of any reference concentration selected from the concentrations (second step). As shown in FIGS. 8A and 8B, a reference function is determined and each of the other functions is multiplied by a ratio to the reference function, so that the multiple functions can be integrated. For this reason, a ratio to the reference function (hereinafter, will be called a concentration correction coefficient α) is determined beforehand for each of the functions. For example, as shown in FIG. 8A, when the function $F_m(r)$ of the medium-concentration sample is used as a reference function, a concentration correction coefficient $\alpha_{hi}$ is determined for the high-concentration sample, a concentration correction coefficient $\alpha_m$ is determined for the medium-concentration sample, and a concentration correction coefficient $\alpha_{lo}$ is determined for the low-concentration sample, the following relationship is established:

$$\alpha_{hi} = \frac{F_m(r)}{F_{hi}(r)}, \alpha_m = \frac{F_m(r)}{F_m(r)} = 1, \alpha_{lo} = \frac{F_m(r)}{F_{lo}(r)} \quad \text{[Expression 1]}$$

The concentration correction coefficient α has a constant value regardless of a distance r from the optical axis. By determining the concentration correction coefficients $\alpha_{hi}$ and $\alpha_{lo}$ satisfying this relationship, $F_{hi}(r)$ and $F_{lo}(r)$ can be integrated with $F_m(r)$.

Figure 9:
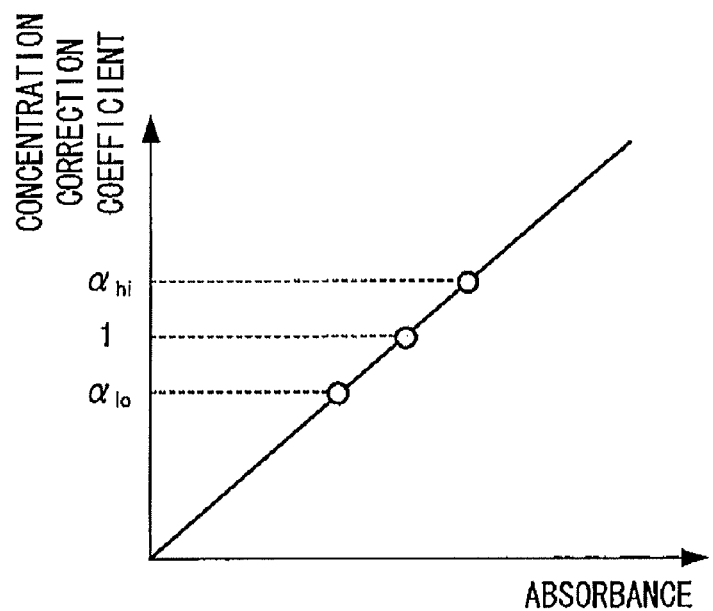
FIG. 9 is an explanatory drawing showing another step of the analyzing method according to the fourth embodiment.

Next, as shown in FIG. 9, the concentration correction coefficients $\alpha_{hi}$ and $\alpha_{lo}$ obtained at the respective concentrations are plotted relative to absorbance and make a rectilinear approximation (third step). In this case, an index (concentration information) indicating a concentration is absorbance proportionate to a concentration (Lambert-Beer law). Based on an obtained rectilinear approximation result, correction coefficients α corresponding to all the respective concentrations can be calculated. By using the luminance of a measured portion (obtained luminance) and background luminance that is reference luminance before a change, the absorbance is determined as follows:

Measured portion absorbance = [Expression 2]
$$\log_{10}\left(\frac{\text{Background luminance}}{\text{Measured portion luminance}}\right)$$

Next, a correction function $g_m(r)$ of the dependence on a filter incident angle is calculated according to the reference concentration based on the luminance distribution $F_m(r)$ of the reference concentration (fourth step). This method has been described in the third embodiment and thus the explanation thereof is omitted.

The following will discuss the steps of measurement.

Figure 10:
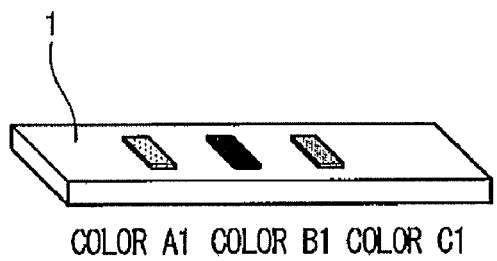
FIG. 10 is a perspective view showing a test piece to be measured in the analyzing method according to the fourth embodiment.

FIG. 10 shows the test piece to be measured. Three color portions (color A1, color B1, and color C1) are spaced at given intervals on the test piece 1, and the concentrations of the samples 7 to be measured in the respective color portions are unknown.

Figure 11A:
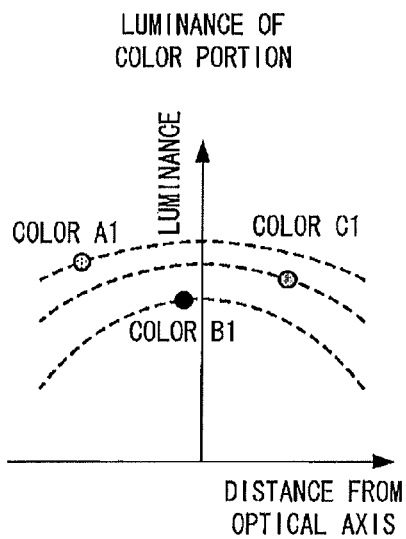
FIG. 11A is an explanatory drawing showing another step of the analyzing method according to the fourth embodiment.
Figure 11B:
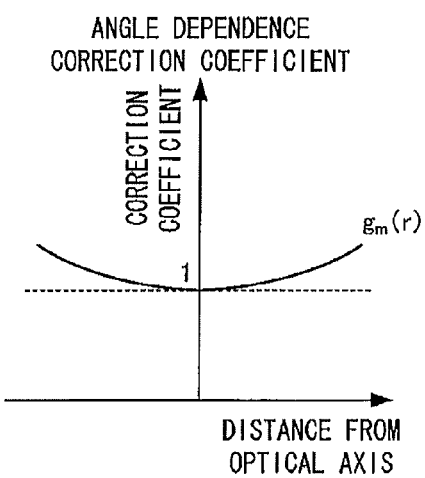
FIG. 11B is an explanatory drawing showing another step of the analyzing method according to the fourth embodiment.
Figure 11C:
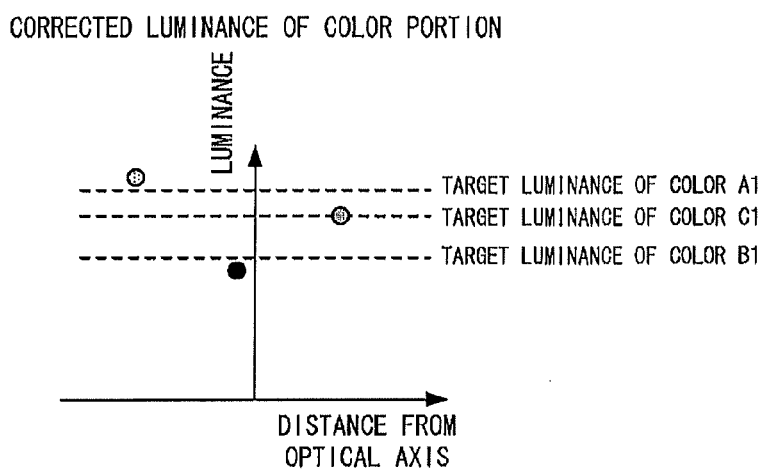
FIG. 11C is an explanatory drawing showing another step of the analyzing method according to the fourth embodiment.

In the color portions on the test piece 1, luminance of the sample 7 is corrected by the correction function $g_m(r)$ of the dependence on a filter incident angle, the correction function $g_m(r)$ being obtained in the fourth step according to the reference concentration. The concentration information is calculated by using the corrected luminance (fifth step). Referring to FIGS. 11A to 11C, the luminance of the color A1, the color B1, and the color C1 is obtained by the image sensor and is affected by the dependence on a filter incident angle according to the concentrations (see FIG. 11A). The angle dependence correction function $g_m(r)$ having been calculated in the fourth step is integrated to the luminance of the color portions, and the dependence on a filter incident angle is corrected (see FIG. 11B), so that luminance somewhat close to true values can be obtained (see FIG. 11C). By applying the obtained luminance of the color portions to (formula 2), absorbance $Z_{A1}$, $Z_{B1}$, and $Z_{C1}$ of the color portions is calculated.

Figure 12:
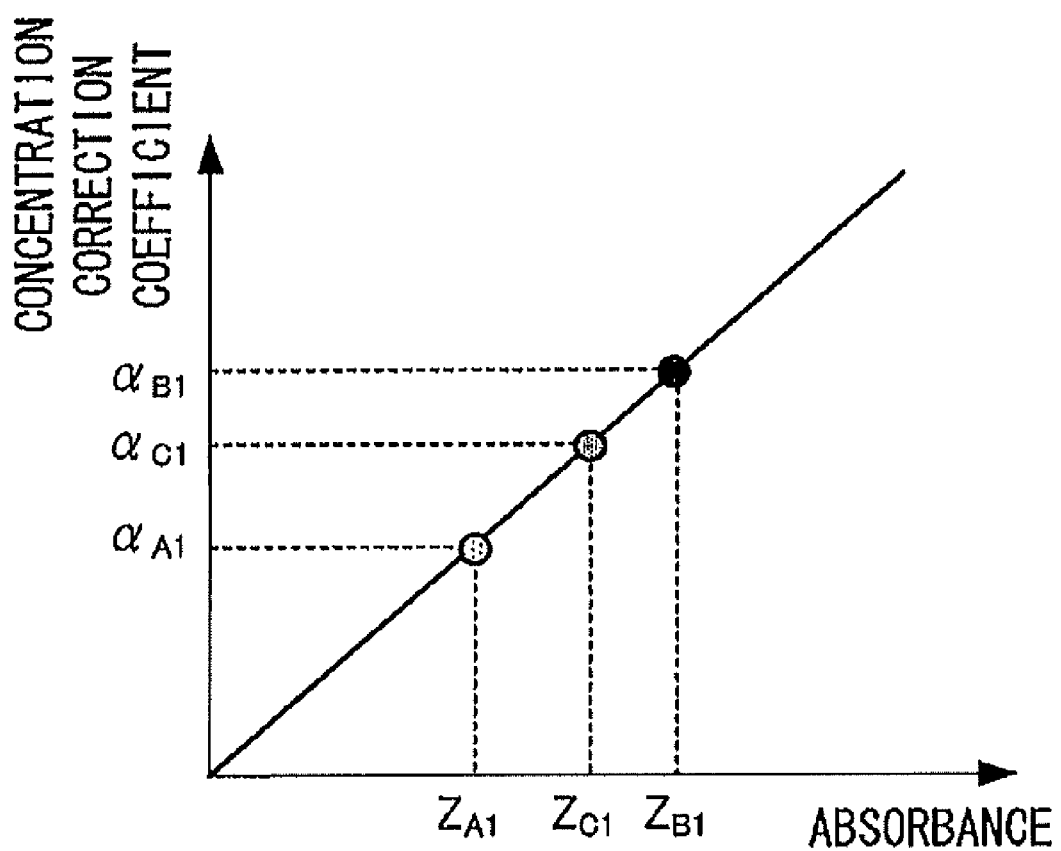
FIG. 12 is an explanatory drawing showing another step of the analyzing method according to the fourth embodiment.

The absorbance obtained in the fifth step is correlated with a straight line determined in the third step, so that the concentration correction coefficients of the samples 7 to be measured with the unknown concentrations are obtained (sixth step). In other words, as shown in FIG. 12, concentration correction coefficients $\alpha_{A1}$, $\alpha_{B2}$, and $\alpha_{C1}$ corresponding to the absorbance $Z_{A1}$, $Z_{B1}$, and $Z_{C1}$ are determined with reference to a previously determined approximate straight line (FIG. 9).

Figure 13A:
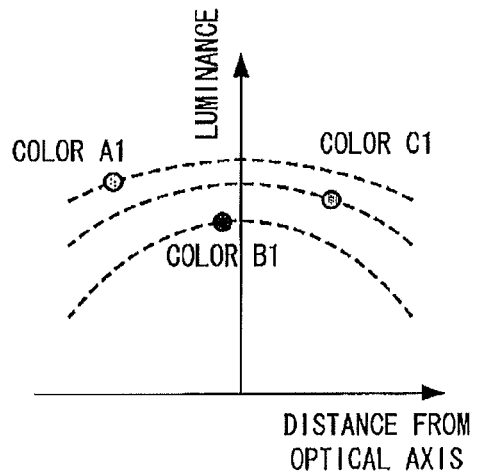
FIG. 13A is an explanatory drawing showing another step of the analyzing method according to the fourth embodiment.
Figure 13B:
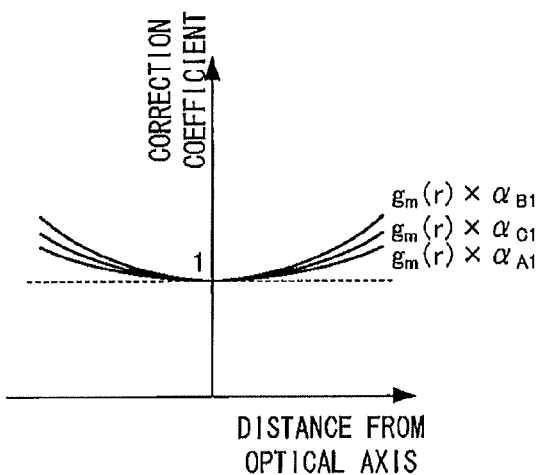
FIG. 13B is an explanatory drawing showing another step of the analyzing method according to the fourth embodiment.
Figure 13C:
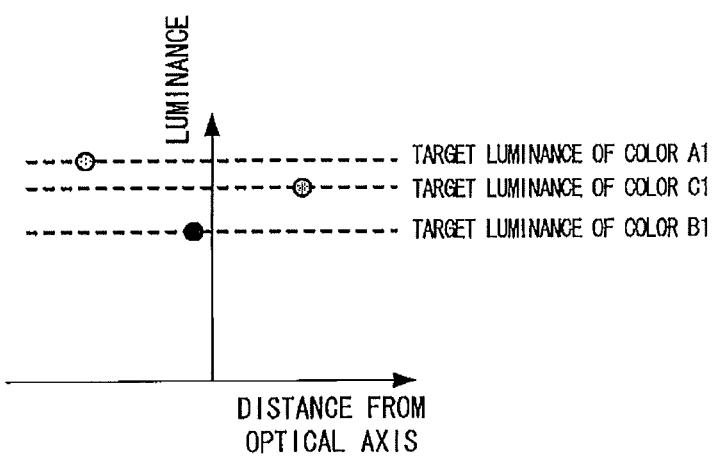
FIG. 13C is an explanatory drawing showing another step of the analyzing method according to the fourth embodiment.

The concentration correction coefficients obtained in the sixth step are integrated to the correction function of the dependence on a filter incident angle, the correction coefficient being determined in the fourth step according to the reference concentration, the luminance of the samples 7 to be measured is corrected by using the correction functions after the integration, and the concentration information of the samples 7 to be measured is obtained again by using the corrected luminance (seventh step). In other words, as shown in FIGS. 13A to 13C, the concentration correction coefficients $\alpha_{A1}$, $\alpha_{B1}$, and $\alpha_{C1}$ corresponding to the concentrations of the colors A1, B1, and C1 are integrated to the angle dependence correction coefficient $g_m(r)$ (see FIG. 11B) determined based on the reference function $F_m(r)$ of the prior art, and the coefficients are integrated to the luminance values of the colors A1, B1, and C1. Thus the luminance of the colors A1, B1, and C1 can be corrected according to the concentrations. Target luminance in FIG. 13C is values having been corrected according to the concentrations.

After that, absorbance is determined again based on the corrected values (target luminance), so that the concentration information of the samples 7 in the colors A1, B1, and C1 is obtained. The sixth step and the seventh step are repeated several times by using the obtained absorbance, so that the absorbance can be determined with higher accuracy.

As previously mentioned, it is possible to correct the dependence on a filter angle at all the concentrations, thereby reducing an error caused by the dependence on a filter angle.

(Fifth Embodiment)

Figure 14:
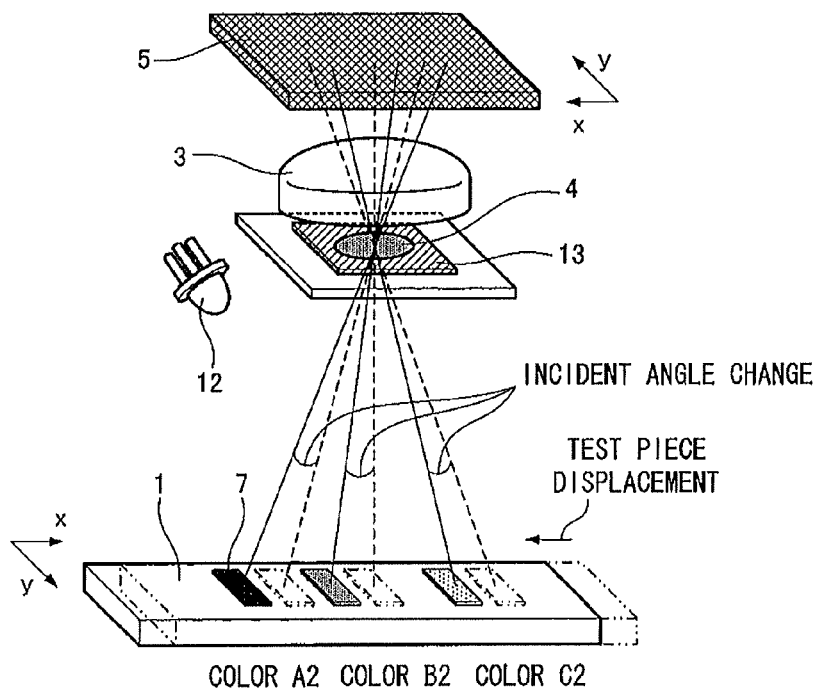
FIG. 14 is an explanatory drawing showing a step of an analyzing method according to a fifth embodiment of the present invention.

Referring to FIGS. 14 to 20, an analyzing device and an analyzing method according to a fifth embodiment of the present invention will be described below. The configuration of the analyzing device shown in FIG. 14 is substantially identical to that of the analyzing device of the fourth embodiment.

Figure 15:
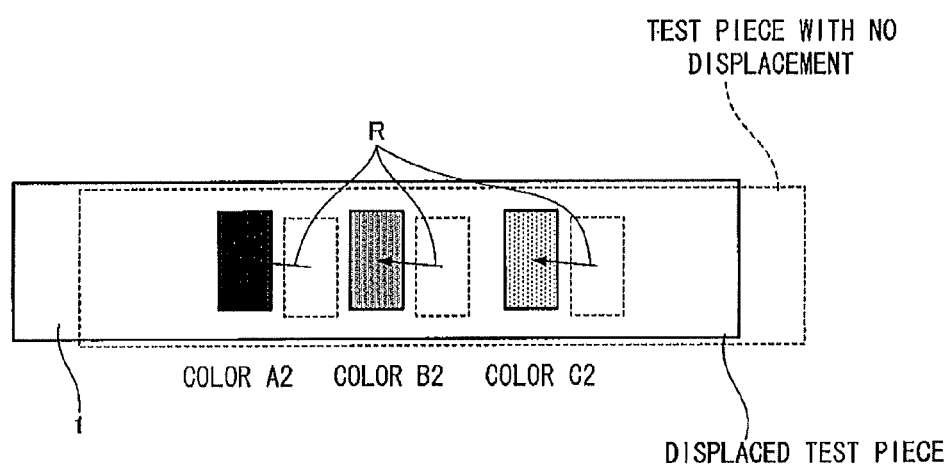
FIG. 15 is a plan view showing a test piece to be measured in the analyzing method according to the fifth embodiment.

In FIGS. 14 and 15, color portions (color A2, color B2, and color C2) on a test piece 1 have samples 7 of different concentrations (the color A2 has a high concentration, the color B2 has a medium concentration, and the color C2 has a low concentration) and the color portions have been displaced by R because of a displacement of the test piece 1 upon setting.

During analysis, calibration curve information is obtained beforehand that contains values measured at several concentrations at the respective positions of the colors A2, B2, and C2 on the test piece serving as a base, and the concentrations are changed by using the calibration curve information during analysis, thereby reducing the influence of the dependence of an optical filter on an angle.

Figure 16A:
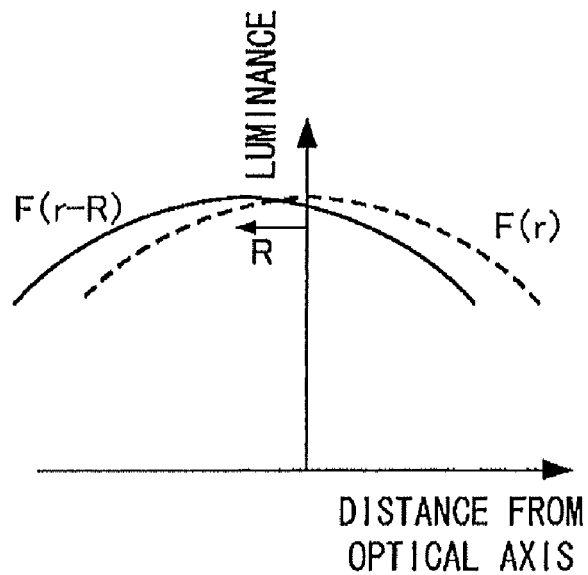
FIG. 16A is an explanatory drawing showing another step of the analyzing method according to the fifth embodiment.
Figure 16B:
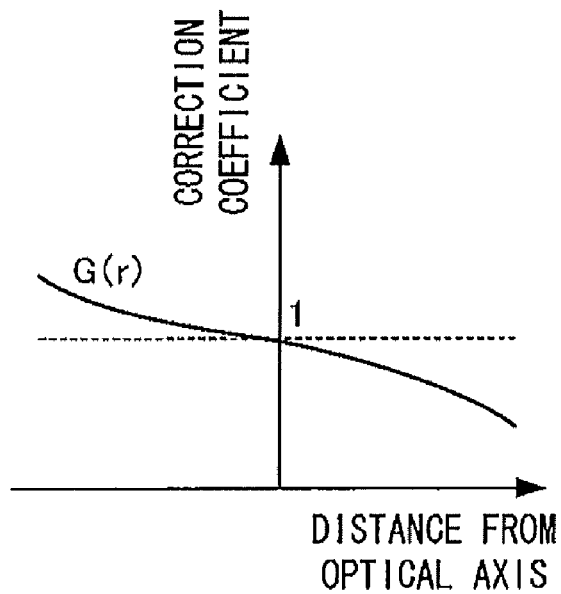
FIG. 16B is an explanatory drawing showing another step of the analyzing method according to the fifth embodiment.

As shown in FIGS. 16A and 16B, because of the displacement, correction function $G(r)$ ($=F(r-R)/F(r)$) is determined by using luminance function $F(r)$ with no displacement and luminance function $F(r-R)$ with the displacement R, and a correction is made by the correction function.

Figure 17:
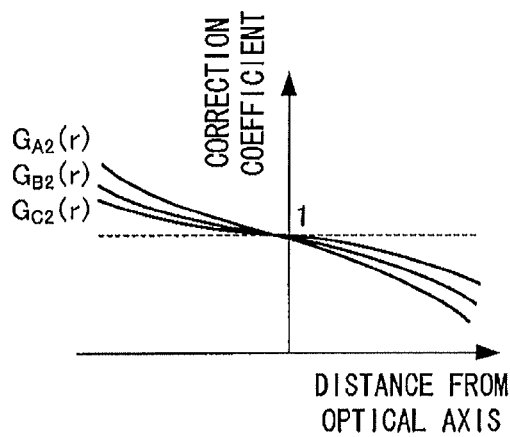
FIG. 17 is an explanatory drawing showing another step of the analyzing method according to the fifth embodiment.

Since this method is suitable for a sample having a single concentration, correction functions $G_{A2}(r)$, $G_{B2}(r)$, and $G_{C2}(r)$ are determined as shown in FIG. 17 according to the concentrations of the colors A2, B2, and C2.

Figure 18:
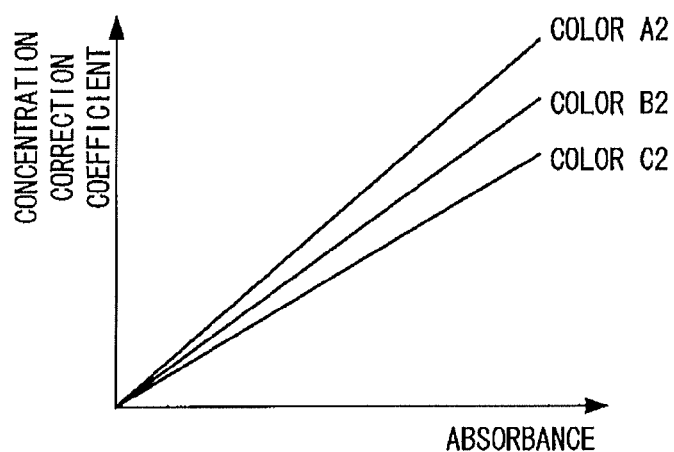
FIG. 18 is an explanatory drawing showing another step of the analyzing method according to the fifth embodiment.

To this end, approximate straight lines for the respective color positions are determined beforehand as shown in FIG. 18. In the fifth embodiment, luminance affected by the influence of dependence on an angle is used as it is. Thus the approximate straight lines are determined for the respective color positions as shown in FIG. 18. Thus a concentration correction coefficient α is determined by the same method as in the fourth embodiment.

Figure 19:
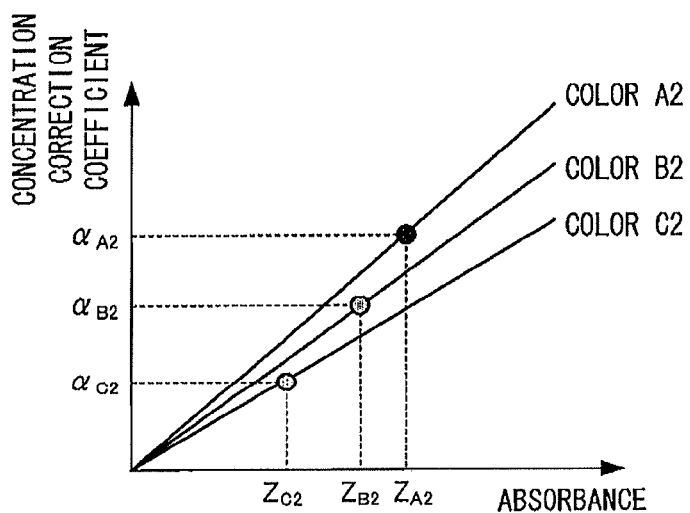
FIG. 19 is an explanatory drawing showing another step of the analyzing method according to the fifth embodiment.

Further, assumed absorbance ($Z_{A2}, Z_{B2}, Z_{C2}$) is determined based on luminance obtained in the colors A2, B2, and C2 (luminance affected by the influence of the dependence on an angle is used as it is). As shown in FIG. 19, concentration correction coefficients $\alpha_{A2}, \alpha_{B2}$, and $\alpha_{C2}$ corresponding to the absorbance $Z_{A2}, Z_{B2}/Z_{C2}$ of the colors A2, B2, and C2 are obtained with reference to the determined approximate straight lines (see FIG. 18) and $G_{A2}(r)$, $G_{B2}(r)$, and $G_{C2}(r)$ are calculated using the concentration correction coefficients as follows:

$$G_{A2}(r) = \alpha_{A2}(G_m(r)-1)+1$$

$$G_{B2}(r) = \alpha_{B2}(G_m(r)-1)+1$$

$$G_{C2}(r) = \alpha_{C2}(G_m(r)-1)+1 \quad \text{[Expression 3]}$$

where $G_m(r)$ is a correction function obtained using the characteristics of a reference function $F_m(r)$. The characteristics of the reference function $F_m(r)$ are used also for preparing the calibration curves.

Figure 20A:
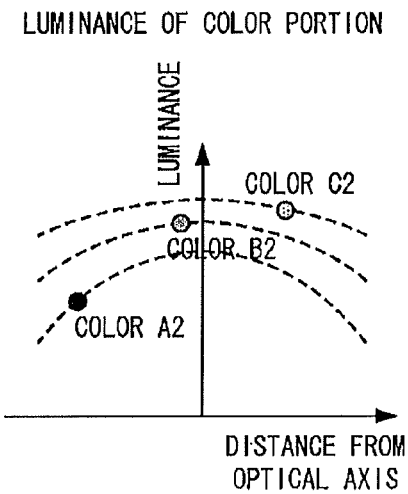
FIG. 20A is an explanatory drawing showing another step of the analyzing method according to the fifth embodiment.
Figure 20B:
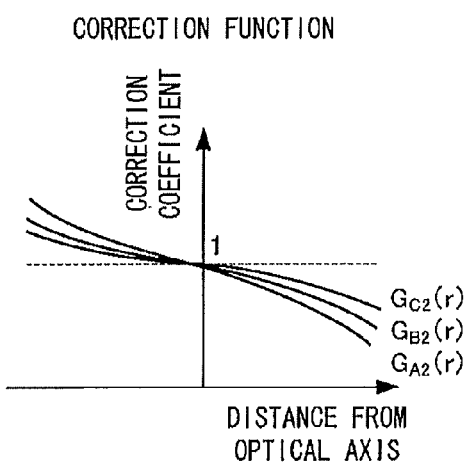
FIG. 20B is an explanatory drawing showing another step of the analyzing method according to the fifth embodiment.
Figure 20C:
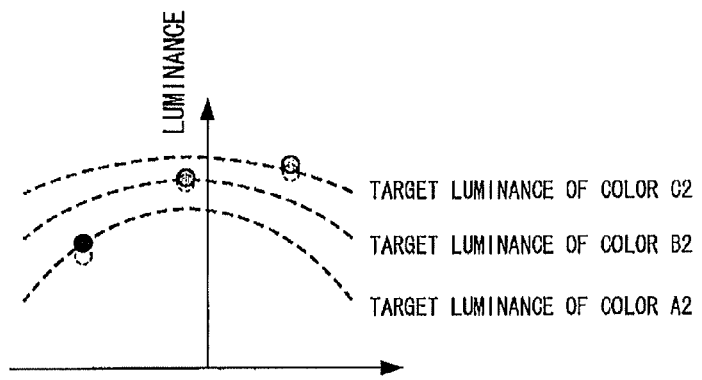
FIG. 20C is an explanatory drawing showing another step of the analyzing method according to the fifth embodiment.

Next, as shown in FIGS. 20A to 20C, the correction functions $G_{A2}(r)$, $G_{B2}(r)$, and $G_{C2}(r)$ corresponding to the concentrations of the colors A2, B2, and C2 are integrated to the luminance values obtained in the colors A2, B2, and C2. Thus the luminance of the colors A2, B2, and C2 can be corrected according to the respective concentrations. Target luminance in FIG. 20C is values corrected according to the concentrations.

After that, absorbance is determined again based on the corrected values (target luminance) and the concentration information of the samples in the colors A2, B2, and C2 is obtained based on the absorbance.

Thus it is possible to correct a displacement of the test piece at all the concentrations, thereby reducing an error caused by the displacement.

In the foregoing embodiments, the luminance values are corrected by using the correction coefficients, the absorbance corresponding to the corrected luminance values is determined, and the concentration information of the samples 7 is obtained based on the absorbance. The correcting method is not particularly limited. Digital data corresponding to the luminance values may be corrected and the concentration information of the samples 7 may be obtained based on the corrected data.

The present invention relates to an analyzing device and is particularly suitable for biochemical analysis. The application of the present invention is not limited and thus the present invention is applicable to various analyzing devices in which light from a sample fixed on a test piece is captured by a photo detector element through an optical system and concentration information is obtained.

Further, the analyzing method and the analyzing device of the present invention have the function of reducing a measurement error caused by the dependence of the optical filter on an incident angle, and the present invention is particularly useful for a biochemical analyzing method and a biochemical analyzing device in which concentrations have to be detected with high accuracy.

Moreover, the analyzing method and the analyzing device of the present invention can reduce a measurement error caused by variations in the concentration of the sample, and have the function of reducing a measurement error caused by a color displacement or the dependence of the optical filter on an incident angle. Thus the present invention is particularly useful for a biochemical analyzing method and a biochemical analyzing device in which concentrations have to be detected with high accuracy.

The invention claimed is:

1. An analyzing method in which light from a sample set on a test piece is received by an image sensor having multiple pixels through an optical system having an optical filter and concentration information of the sample is obtained, the analyzing method comprising:
 a first step of calculating beforehand a luminance value obtained at any position in the image sensor based on dependence on a filter incident angle and wavelength characteristics of the light from the sample set with various known concentrations on the test piece;
 a second step of calculating correction coefficients for matching luminance distributions obtained at the respective concentrations in the first step with a luminance distribution of any reference concentration selected from the concentrations;
 a third step of making a rectilinear approximation by plotting the correction coefficients obtained at the respective concentrations in the second step, relative to the concentration information,
 a fourth step of calculating a correction function of the dependence on a filter incident angle according to the reference concentration, based on the luminance distribution of the reference concentration;
 a fifth step of correcting luminance obtained on the samples separately set to be measured with unknown concentrations on the test piece, by using the correction function obtained in the fourth step according to the reference concentration, and calculating the concentration information by using the corrected luminance;
 a sixth step of obtaining concentration correction coefficients of the samples to be measured, by correlating the concentration information obtained in the fifth step with a straight line determined in the third step; and
 a seventh step of integrating the concentration correction coefficients obtained in the sixth step to the correction function obtained in the fourth step according to the reference concentration, correcting the luminance of the samples to be measured, by using the correction functions after the integration, and obtaining again the concentration information of the samples to be measured, by using the corrected luminance.

2. An analyzing device in which light from a sample set on a test piece is received by an image sensor having multiple pixels through an optical system having an optical filter and concentration information of the sample is obtained, the analyzing device comprising:

a luminance calculator for calculating a luminance value beforehand at any position in the image sensor based on dependence on a filter incident angle and wavelength characteristics of the light from the sample set with different known concentrations on the test piece;

a first correction coefficient calculator for calculating correction coefficients for matching luminance distributions obtained at the respective concentrations by the luminance calculator with a luminance distribution of any reference concentration selected from the concentrations;

a rectilinear approximation unit for making a rectilinear approximation by plotting the correction coefficients obtained at the respective concentrations by the first correction coefficient calculator, relative to the concentration information;

a correction function calculator for calculating a correction function of the dependence on the filter incident angle according to the reference concentration, based on the luminance distribution of the reference concentration;

a concentration calculator for correcting luminance obtained on the samples separately set to be measured with unknown concentrations on the test piece, by using the correction function obtained by the correction function calculator according to the reference concentration, and calculating the concentration information by using the corrected luminance;

a second correction coefficient obtaining unit for obtaining concentration correction coefficients of the samples to be measured, by correlating the concentration information obtained by the concentration calculator with a straight line determined by the rectilinear approximation unit; and a concentration obtaining unit for integrating the concentration correction coefficients obtained by the second correction coefficient obtaining unit to the correction function obtained by the correction function calculator according to the reference concentration, correcting the luminance of the samples to be measured, by using the correction functions after the integration, and obtaining again the concentration information of the samples to be measured, by using the corrected luminance.

* * * * *